US006982083B1

(12) United States Patent
D'Hulst et al.

(10) Patent No.: US 6,982,083 B1
(45) Date of Patent: Jan. 3, 2006

(54) STARCH GRANULES CONTAINING A RECOMBINANT POLYPEPTIDE OF INTEREST, METHOD FOR OBTAINING THEM, AND THEIR USES

(75) Inventors: Christophe D'Hulst, Wattrelos (FR); Steven Ball, Bourghelles (FR)

(73) Assignee: Centre National de la Recherche Scientifique, (FR)

( * ) Notice: Subject to any disclaimer, the term of this patent is extended or adjusted under 35 U.S.C. 154(b) by 0 days.

(21) Appl. No.: 09/980,771

(22) PCT Filed: May 19, 2000

(86) PCT No.: PCT/FR00/01384

§ 371 (c)(1),
(2), (4) Date: Jan. 10, 2002

(87) PCT Pub. No.: WO00/71734

PCT Pub. Date: Nov. 30, 2000

(30) Foreign Application Priority Data

May 21, 1999 (FR) .................................. 99 06494

(51) Int. Cl.
*A61K 38/51* (2006.01)
*C12N 9/00* (2006.01)
*C12N 9/10* (2006.01)
*C12N 1/20* (2006.01)
*C07H 21/04* (2006.01)

(52) U.S. Cl. .............................. 424/94.5; 435/4; 435/6; 435/69.1; 435/183; 435/193; 435/194; 435/252.3; 435/320.1; 424/94.1; 536/23.2

(58) Field of Classification Search ................ 435/183, 435/193, 4, 6, 194, 252.3, 320.1, 69.1; 530/350; 536/23.2; 424/94.1, 94.5
See application file for complete search history.

(56) References Cited

FOREIGN PATENT DOCUMENTS

| WO | 9745545 | 12/1997 |
| WO | 9814601 | 4/1998 |

OTHER PUBLICATIONS

Isshiki et al, "A Naturally . . . First Intron", The Plant Journal, Jul. 1998, vol. 1, pp. 133-138.
Database Swissprot 'en ligne!, Aug. 1, 1998, D'Hulst et al, "Cloning . . . reinhardtii", XP002146121, Accession No. 064925.
Database EMBL Sequence Library 'en ligne!, Jun. 2, 1998, D'Hulst et al, "Cloning . . . reinhardtii", XP002146137, Accession No. AF026420.
Delrue et al "Waxy . . . Amylopectin", Journal of Bacteriology, US, Washington. D.C., vol. 174, No. 11, Jun. 1, 1992, pp. 3612-3620.
Chen et al, "Improved . . . Glucoamylase", Biotechnology Progress, vol. 7, 1991, pp. 225-229, XP002056940.
Kusnadi et al "Functional . . . *coli*", GENE, vol. 127, 1993, pp. 193-197 XP002056413.
Mu-Forster et al, "Physical . . . Endosperm", Plant Physiology, vol. 111, 1996, pp. 821-829, XP002056414.
Maddelein et al, "Toward . . . Synthesis", The Journal of Biological Chemistry, vol. 269, No. 40, 1994, pp. 25150-25157.
Dauvillee et al, "Novel . . . reinhardtii", Plant Physiology, Jan. 1999, vol. 119, No. 1, pp. 321-330.

*Primary Examiner*—Manjunath N. Rao
(74) *Attorney, Agent, or Firm*—Charles A. Muserlian

(57) ABSTRACT

The present invention relates to starch granules containing a fusion polypeptide between a starch synthase and a recombinant polypeptide of interest, the nucleotide sequences used for obtaining them, their methods of preparation, as well as their uses, especially in pharmaceutical compositions.

13 Claims, 8 Drawing Sheets

Figure 1

Figure 1 (continued)

```
AAAGAAGAGTAACGAAACTGTAGCAGTAGCAGAGCCACTTGCGCGGCGGGCGGGCGACCACGGCCCGGCCCGGCCCTGTCCTGCCCTCAGCCTTGTGATTC
TTTCTTCTCATTGCTTTGACATCGTCATGCTCGTGAACGCGCCGGCCCGGCCCGGCCCGGCACGCGTGTGCGGCGGGACAGGACGGGAGTCGGAACACTAAG
GGCGGCAAGAGGGCGGGTCTGTACACTCCATCCATTCCAGGATTTTGCAGGCTGCCTGAGAGTTTGCCATTTGTGGGACGTGAGCGGCGGACGGCCG
CCGCCGTTCTCCCGCCAGACATGTGAGGTAGGTAAGGTCCTAAAAACGTCCGACGGACTCTCAAACGTAAAACACCCTGCACTCGCCGCCCTGCCGGC
CGCCGGGCTCTCCTACCGCCTCCGGCAACGGAGAAGTGGGAGGCGCTGTAGCCCGGTGACCCCCCAATGTAGAGGATGGGATACATAAGAGCGTGTGGAA
GCGGCCCCGAGAGAGGATGGCGGAGCCGTTGCCCTCTTCACCCTCCGGACACTCGGGGCCCACTGGGGGGTTACATCTCCTACCCTATGTATTCTCGCACACCTT
TGGTGGTAAAAGAGGAGGGGCCTGGGTCGCCCTCGATGGTTTTGTTGAGGTGCAGACGGCACCGTCGGCGTCAAAGGCCCTCGCAAGGCCCGGGTGCCT
ACCACCATTTCTCCTCCCCGGACCCAGCGGGGAGCTACCAAAACAACTCCACGTCTGCCGTGCCAGCCGCAGTTCCGGGAGCCGTTCCGGCCCACGGA
TGGGCTCATTTTTGGTGCCCGTCGATGATGAGAGATTGGCCAGCGGTTTTTGAGGCTGGCTCGAAGCGAGGGTTTGTGGAAGTGGAGCGAGGAGGGTTG
ACCCGAGTAAAAACCACGGGCAGCTACTACTCCTAACCGTCGCCAAACACTTCGCTGCGACCGAGCTTCGCTCCGAGCTTCGCTCCAACACCTTCACCTCGCTCTCCCAAC
GAGAAAGAGGCCGACATGCTTGACTGGAGTACACAAAGTGGAGCGTGCGACGGCACGGAGGCATTGGCGACTATTGACCCAGTAGTGTGAAAGTAGT
CTCTTTCTCCGCCTGTACGAACTGACCTGTTTCACCTGCGCCTCCGTAACCGCCTGATAACTGGGTCATCACACCTTTCATCA
TGGACCTGAATTCTTTGAGAGTACCGCCGCATTAATCCGTGAGAGTAACAAAGATGGCACCTGAAAAAAAAAAAAAAAAAAAAAAAA
ACCTGGACTTAAGAAACTCTCATTGTTTCTACCGTGACTTTTTTTTTTTTTTTTTTTTTTTTTTT
```

Figure 2

Figure 2 (continued 1)

```
TACCTGGACAACCACAAGCGCTTCGCCCTGTTCTGCAAGGCCGCTATTGAGGCTGCCGCTGCCCTTCGGCCCCGGAGGACTGCGTCTTCGTGG
ATGGACCTGTTGGTGTTCGCGAAGCGGGACAAGACGTTCCGGCGATAACTCCGACGGGCAAGCCGGGGCCGTCCTGACGCAGAAGCACC
  Y  L  D  N  H  K  R  F  A  L  F  C  K  A  A  I  E  A  A  R  V  L  P  F  G  P  G  E  D  C  V  F  V
                                   ─── coding sequence of the cDNA of the GBSSI CCAACGACTGGCACTCCGCCCTGGTGCCCGTCCTCGTCTGAAGGACGAGTACCAGCCCAAGGGCCAGTTCACCAAGGCCAAGTCGGTGCTGGCTATCCACAA
GGTTGCTGACCGTGAGGCGGGACCACGGCAGGACGAGGACTTCCTGCTCATGGTCGGGTTCCCGGTCAAGTGGTTCAGCCACGACCGATAGGTGTT
  A  N  D  W  H  S  A  L  V  P  V  L  L  K  D  E  Y  Q  P  K  G  Q  F  T  K  A  K  S  V  L  A  I  H  N
                                     ─── coding sequence of the cDNA of the GBSSI CATCGCCTTCCAGGGCCGCATGTGGGAGGAGGCTTTCAAGGACACGAAGCTGCCCAGGCCGCCTTTGACAAGCTGGCCTTCTCGGACGGCTATGCCAAG
GTAGCGGAAGGTCCCGGCGTACACCCTCCTCCGAAAGTTCCTGCTTCGACGGGTCCGGCGGAAACTGTTCGACCGGAAGAGCCTGCCGATACGGTTC
  I  A  F  Q  G  R  M  W  E  E  A  F  K  D  T  K  L  P  Q  A  A  F  D  K  L  A  F  S  D  G  Y  A  K
                                     ─── coding sequence of the cDNA of the GBSSI GTTTACACTGAGGCCACCCCCATGGAGGAGGACGAGAAGCCCCCGCTGACGGGAAAGACCTACAAGAAGATCAACTGGCTGAAGGGTGGCATTATCGCCG
CAAATGTGACTCCGGTGGGGTACCTCCTCCTGCTCTTCGGGGGCGACTGCCCTTCTGGAGCTGCCCTTTCTGGATGTTCTTCTTCTAGTTGACGACTTCCCACCGTAATAGCGGC
  V  Y  T  E  A  T  P  M  E  E  D  E  K  P  P  L  T  G  K  T  Y  K  K  I  N  W  L  K  G  G  I  I  A
                                     ─── coding sequence of the cDNA of the GBSSI CCGACAAGCTGGTGACTGTGTCGCCCAACTACGCGACCGAGATCGCTGCCGATGCCGCGGGTGTGGAGCTGGACACCGTCATCCGCGCCAAGGGCAT
GGCTGTTCGACACTGACACTGACAGCGGGTTGATGCGCGGTTCTCTAGCGCCGGCCGCCACCTGTGGCAGTAGGCGCGGTTCCCGTA
  A  D  K  L  V  T  V  S  P  N  Y  A  T  E  I  A  A  D  A  A  G  G  V  E  L  D  T  V  I  R  A  K  G  I
                                   ─── coding sequence of the cDNA of the GBSSI TGAGGGCATTGTGAACGGGCATGGACATTGAGGACGAGGTGAACCCCAAGACCGACAAGTTCCTGTCTGCGCCCTACGACCAGAACAGCGTCTACGGCCGGCAAG
ACTCCCGTAACACTTGCCGTACCTGTAACTCCTCACCTTGGGGTTCTGTTCAAGGACAGACGCGGGATGCTGGTCTTGTCGCAGATGCGGCCGTTC
  E  G  I  V  N  G  M  D  I  E  E  W  N  P  K  T  D  K  F  L  S  A  P  Y  D  Q  N  S  V  Y  A  G  K
                                   ─── coding sequence of the cDNA of the GBSSI
```

Figure 2 (continued 2)

Figure 2 (continued 3)

```
GAGGTGGTGTACGGCAAGGGCGGCGTGGCCACCCGCCAAGAAGGAGGAGATCAAGGTGCCCGTTGCCGAGAAGATCCCCGGCGACCTGCCCGCCGTGTCCT
CTCCACCACATGCCGTTCCCGCCGCACCGTGGCGGTTCTTCCTCCTCTAGTTCCACGGGCAACGGCTCTTTCTAGGGGCCGCTGGACGGGCGGCACAGGA
  E   V   V   Y   G   K   G   G   V   A   T   A   K   K   E   E   I   K   V   P   V   A   E   K   I   P   G   D   L   P   A   V   S
                                                 coding sequence of the cDNA of the GBSSI ACGCCCCCAACACCCTGAAGCCCGTGTCCGCTCTCCGTGGAGGGCCACCCGCCGCGCCCAAGGTCGGCACCACCGCGCCCCGCGCCATGGGCGCGTGGCG
TGCGGGGGTTGTGGGACTTCGGGCACAGGCGGAGGCACCTCCCGTTGCCGCGGGGCGCGGGTTCAGCGTGGTGGCGGGGCGGTACCCGCGCACCGC
  Y   A   P   N   T   L   K   P   V   S   A   S   V   E   G   N   G   A   A   A   P   K   V   G   T   T   A   P   A   M   G   A   W   R
                                                       coding sequence of the cDNA of the GBSSI CGGCGACCACCCCCTCGGGCCCCTCGCCGCGCCACCCCCAAGGTGACCACCTACAAGCCCGCCTGCCCGCCACCGCCAAGCCCAAGACCGCTGGC
GCCGCTGGTGGGGGAGCCCGGGGAGCGCGGGGCCGGGGAGCGGGCCGGTGGGGTTCCACTGGTGGATGTTCGGGCGGGACGGGCCGGTGGCGGTTCGGGTTCTGGCGACCG
  A   T   T   P   S   G   P   S   P   A   A   A   T   P   K   V   T   T   Y   K   P   A   L   P   A   T   A   K   P   K   T   A   G
                                                      coding sequence of the cDNA of the GBSSI CTCAAGCTGGCCGGTGAGGCCTCCACCACCTCGAGAACGGCGTGCCTCCAACGGCAACGGCAACGGTGCCTCGGCCTCCAAGACCTCGGCTG
GAGTTCGACCGGCCACTCCGGAGGTGGTGGAGCTGGAGCTCTTGCCGCGACGGAGGTTGCCGTTGCCAGGAGCCGGAGGTTCTGGAGCCGAC
  L   K   L   A   G   E   A   S   T   T   S   T   S   E   N   G   A   A   S   N   G   N   G   A   S   K   T   S   A
                                                 coding sequence of the cDNA of the GBSSI CCAAGCCCCTGGTCTCCGCCGCCACCCGCAAGTCCGCCTAAAGCGGCAGTAGCCGCAGAGGCGGCGACAGCATGAGCGGTCGACCAAAGCTGTGGCAGG
GGTTCGGGGACCAGAGGCGGCGGTGGGCCGTTCAGGCGGTGGGCGTTCAGGGCGGATTTTCGCCGTCATCGGCGCGCTGTCGTACTCGCCGAGCTGGTTTCGACACCGTCC
  L   K   P   L   V   S   A   A   T   R   K   S   A
     coding sequence of the cDNA of the GBSSI AACGGCTGTAGCAGCGGCAGGGCGGCGCCACCGGCGAGGAGCAGGCTTGCGGCAGGAGGGCGATGAGCTTAGCGGCCGTGAGCATGGCAGGCGGAAACG
TTGCCGACATCGTCGCCGTCGCCGGCGGTGGCCGTCGCCGGCGCTCCTCGTCGTCCGAACGCGTCGCTTCCGCTACTACTGCCGCCACTCGTACCGTCGCCCTTGC
A   K   P
                                        noncoding sequence of the cDNA of the GBSSI
```

Figure 2 (continued 4)

```
TGTGTACTGAAATGTGGTGCATGAGAGTGTCGTCGTCTGTAATGAAGTCGGTTTTGCGAGACCGGAGAAACGCCGGTTTGGTTTTGTAGTGCAGGGCCTGTG
ACACATGACTTTACACCACGTACTCTCACAGCACGACATTACTTCAGCCAAAACGCTCTGGCCTCTTTGCGGCCAAACCAAAACATCACGTCCCGACAC
────────── noncoding sequence of the cDNA of the GBSSI ──────────

GTTTCGGTTTTGCCCAAGTCCAAAAGAAGAGTAACGAAACTGTAGCAGTAGCAGAGCACTTGCGCGGCGGCGACCACGCCGGCCCGTGCGCAGCCTGT
CAAAGCCAAAAACGGGTTCAGGTTTTTCTTCATTGCTTTGACATCGTCATCGTCTCGTCGTCGTGAACGCGCCGCTGGTGCGGCCACGCGTCGGACA
────────── noncoding sequence of the cDNA of the GBSSI ──────────

CCTGCCCCTCAGCCTTGTGATTCGGCGGCAAGAGAGGGCGGGTCTCGTACACTCCATCCATTCCAGGATTTTTGCAGGCTGCCTGAGAGTTTGCCATTTTGTGG
GGACGGGAGTCGGAACACTAAGCGCCGTTCTCCCGCCAGACATGTGAGGTAGGTAAGGTCCTAAAAACGTCCGACGACTCTCAAACGGTAAAACACC
────────── noncoding sequence of the cDNA of the GBSSI ──────────

GACGTGAGCGGCGGGAACGGCGCGCGCGGGCTCTCCTACCGCCTCCGGCAACGGAGAAGTGGGAGGCGCTGTAGCCCGGTGACCCCCAATGTAGAGGATG
CTGCACTCGCCGCCCTGCCGGCGGCCCGGGCCCGAGAGGATGGCGGAGGCCGTTGCCTCTTCACCCTCCGGACATCGGGCCACTGGGGGTTACATCTCCTAC
────────── noncoding sequence of the cDNA of the GBSSI ──────────

GGATACATAAGAGCGTGTGGAATGGTGGTAAAAGAGGAGGGGCCTGGGTCGCCCCTCGATGTTTTGTTGAGGTGCAGACGGCACCGTCGGCGTCAAAGG
CCTATGTATTCTCGCACACCTTACCACCATTTCTCCTCCCCGGACCAGCGGGGAGCTACCAAAACAACTCCACGTCTGCCGTTGGCAGCCGCAGTTTCC
────────── noncoding sequence of the cDNA of the GBSSI ──────────

CCCTCGCAAGGCCCGGGTGCCTTGGGCTCATTTTTGGTGCCCGTCGATGATGAAGATTGGCCAGCGGTTTTTTGAGGCTGGCTCGAAGCGAGGGTTTGT
GGGAGCGTTCCGGGCCACGGAACCCGAGTAAAAACCACGGGCAGCTACTACTCTCTAACCGGTCGCCAAAAAACTCCGACCGAGCTTCGCTCCCAAACA
────────── noncoding sequence of the cDNA of the GBSSI ──────────
```

Figure 2 (continued 5)

```
GGAAGTGGAGGCGAGGAGGGTTGGAGAAAGAGGCGGACATGCTTGACTGGAGGTACACAAAGTGGAGCCGTGCGACGGCACGGAGGCATTGGCGGACTATTG

CCTTCACCTCGCTCCTCCCAACCTCTTTCTCCGCCTGTACGAACTGACCTCCATGTGTTTCACCTCGCACGCTGCCTCCGTAACCGCCTGATAAC
————————— noncoding sequence of the cDNA of the GBSSI ACCCAGTAGTGTGGAAAGTAGTTGGACCTGAATTCTTTGAGAGTACCGCGCATTAATCCGTGAGAGAGTAACAAAGATGGCACCTGAAAAAAAAAAA TGGGTCATCACACCTTTCATCAACCTGGACTTAAGAAACTCTCATGGCGCGTAATTAGGCACTCTCTCATTGTTTCTACCGTGGACTTTTTTTTTTTT
————————— noncoding sequence of the cDNA of the GBSSI

AAAAAAAAAAAAAAAA
————→ 3117
TTTTTTTTTTTTTTTT
```

STARCH GRANULES CONTAINING A RECOMBINANT POLYPEPTIDE OF INTEREST, METHOD FOR OBTAINING THEM, AND THEIR USES

This application is a 371 of PCT/FR00/01384 filed May 19, 2000.

The present invention relates to starch granules containing a recombinant polypeptide of interest, a method of obtaining them, as well as their uses, especially in pharmaceutical compositions.

Starch is one of the world's most important sources of polysaccharides, occurring in particular in plants (maize, potato, wheat, rice, barley, etc.), algae, micro-algae etc.

Starch occurs in the form of granules that are insoluble in water, the size of which can vary from 0.1 to several tens of μm in diameter depending on its origin (plants, algae or micro-algae) or even the genotype of the plant in question. Thus, the sizes of these granules vary from 0.1 μm in diameter to more than 50 μm in diameter. Furthermore, the degrees of crystallinity of these granules range from 0% (for granules rich in amylose) to over 30%. There are three or four crystalline types (A, B, C, V). The granule grows by the laying-down of alternately amorphous and semicrystalline layers starting from the centre of the starch granule.

Starch contains several distinct polysaccharide fractions, composed of glucans bound at α-1,4 and branched at α-1,6. More particularly, starch consists of two glucose polymers: amylose on the one hand, the minor fraction of the granule (about 20–30 wt. %), of low molecular weight, with little branching (<1% of α-1,6 bonds) and amylopectin on the other hand, the major fraction of the granule (70–80 wt. %), of high molecular weight and highly branched (5% of α-1,6 bonds). Amylose is not necessary for the development of crystallinity of the starch granule; it is now known that it is amylopectin that is responsible for the crystallinity of the starch granule.

In biological terms, strictly speaking starch only occurs in the plant kingdom, and more specifically in the chloroplasts or in the non-photosynthetic granules of the eukaryotic plant cell. Two types of starch can be synthesized by plants: temporary or photosynthetic starch (synthesis of which takes place at the level of the chloroplasts), and reserve starch (synthesis of which takes place at the level of the amyloplasts).

Synthesis of starch in plants involves a whole panoply of enzymes taking part in biosynthesis of the precursor ADP-glucose, scaffolding of the amylose and amylopectin molecules and, finally, degradation of the starch granule.

The first stage in the biosynthesis of starch is the production of the precursor ADP-glucose with the involvement of the two enzymes: phosphoglucomutase (PGM) and ADP-glucose pyrophosphorylase (AGPase).

The second stage in the biosynthesis of the starch granule also involves two types of enzymes, mainly taking part in the synthesis of amylose and amylopectin: starch synthases (or adenosine diphosphate glucose α-1,4-glucan α-4-glucosyltransferases) and branching enzymes (or α-1,4-glucan-6-glucosyltransferases). The starch synthases catalyse the transfer of the glucose residue from ADP-glucose onto growing chains of glucans by creating an O-glycosidic bond of type α-1,4. Then the branching enzymes hydrolyse an α-1,4 bond of an elongating glucan, and then join the fragment thus released onto the remainder of the glucan by means of an α-1,6 bond.

With regard to starch degradation, there are two main families of degrading enzymes: the hydrolytic enzymes (hydrolases) on the one hand, such as α-amylases (endomylases), β-amylases (exomylases), γ-amylases (amyloglucosidases), D-enzymes (glucosyltransferases), R-enzymes (debranching enzymes), α-glucosidases (maltases) and, on the other hand, the phosphorolytic enzymes (or starch phosphorylases).

Several isoforms of starch synthases occur together in higher plants. The main difference between these isoforms relates to their solubility (i.e. they are dissolved in the plastid stroma in plants) or to the fact that they are bound to the starch granule.

The starch synthases bound to the starch granule (or GBSS: Granule Bound Starch Synthases) occur in close association with starch. Several isoforms of GBSS have been isolated in maize, pea, potato or wheat (MacDonald and Preiss, 1985; Smith, 1990; Dry et al., 1992; Denyer et al., 1995). In all cases, GBSSI is the main isoform; the part played by this isoform in the biogenesis of the starch granule is the formation of amylose (Tsai, 1974; Hovenkamp-Hermelink et al., 1987; Delrue et al., 1992; Denyer et al., 1995). A mutation at the loci WX of cereals, AMF of the potato, and LAM of the pea, combines disappearance of GBSSI with complete collapse of the amylose fraction of starch. A cDNA corresponding to the "Waxy protein" (through a misuse of language, the term "Waxy protein" is employed to designate the GBSSI in plants, thus distinguishing it from other GBSS) has been isolated in wheat, barley, maize, rice, potato and pea. Comparisons of the relative protein sequences show there is considerable homology between the different species (Ainsworth et al., 1993).

GBSSI is not the only starch synthase bound to the starch granule. Other isoforms are found bound to the starch granule in pea, potato, maize or wheat (Smith, 1990; Dry et al., 1992; Mu et al, 1994; Denyer et al, 1995). However, the roles of these various isoforms are not yet clear. Furthermore, most of them are also found in the soluble phase.

The soluble starch synthases (SS) are not bound to the starch granule, but are found in soluble form in the plastid stroma of plants. As with the bound forms, several forms of soluble starch synthases occur in the higher plants. For example, three isoforms of soluble starch synthases (SSI, SSII and SSIII) have been detected in the potato tuber.

cDNA's corresponding to various forms of soluble starch synthases have been cloned in higher plants (Baba et al, 1993; Dry et al, 1992; Edwards et al, 1995; Abel et al, 1996; Marshall et al, 1996; Gao et al, 1998). Sequence comparison flowing from this clearly shows the presence of three regions that are highly conserved across the isoforms, whether within a single species or between species of higher plants.

Recent research by the Inventors made it possible to establish that soluble starch synthase II (SSII) from *Chlamydomonas reinhardtii* is mainly involved in the formation of crystals of the amylopectin molecule.

On the other hand, GBSSI does not take part in the construction of amylopectin crystals. GBSSI activity has never been detected in the soluble phase. GBSSI is intimately associated with the starch granule. However, in contrast to amylase, no unit binding to starch has been found in the GBSSI sequences described so far. Accordingly, the mechanism controlling the binding of GBSSI to the starch granule is unknown.

Starch synthases are of particular interest in that these enzymes might make it possible to transport a recombinant peptide of interest towards the plastids where the biosynthesis of starch granules takes place. Thus, the transformation of plants with sequences coding for fusion peptides between a starch synthase and a peptide of interest would make it possible to obtain starch granules in large quantity, from which the said peptide of interest could be recovered.

It was with this objective that the authors of International Application WO 98/14601 (Exseed Genetics) described nucleotide sequences coding for fusion proteins in which the polypeptide of interest is bound to the amino terminal end of a starch synthase selected from the group comprising soluble starch synthases I, II and III (SSI, SSII, SSIII), granule bound starch synthases (GBSS), branching enzymes I, Ia and IIBb and the glucoamylases. However, no method of transformation of plants by means of the sequences described in that application, and hence of obtaining starch granules transformed by the said sequences, is illustrated in detail.

The present invention arises from the demonstration by the inventors that only the transformation of plants with nucleotide sequences coding for fusion polypeptides in which the polypeptide of interest is bound to the carboxy terminal end of the starch synthase makes it possible to obtain starch granules containing the said peptide of interest.

One of the aims of the present invention is to provide novel nucleotide sequences coding for fusion proteins capable of transporting a peptide of interest towards the site of biosynthesis of the starch granules in plant cells (including the cells of algae or micro-algae).

Another aim of the present invention is to provide plants that have been transformed by means of the aforementioned nucleotide sequences, the said plants producing starch containing a polypeptide of interest.

Another aim of the present invention is to provide starch granules containing a polypeptide of interest.

Another aim of the present invention is to provide a method of preparation of these starch granules.

Another aim of the present invention is to provide a method of preparation of a recombinant polypeptide of interest starting from these starch granules.

Another aim of the present invention is to provide compositions, especially pharmaceutical or for foodstuffs, containing the aforementioned starch granules.

Another aim of the present invention is to provide a method of biotransformation of starch granules when the said peptide of interest that is used is capable of transforming starch.

The invention will be illustrated below with the aid of the following diagrams:

Figure 1:
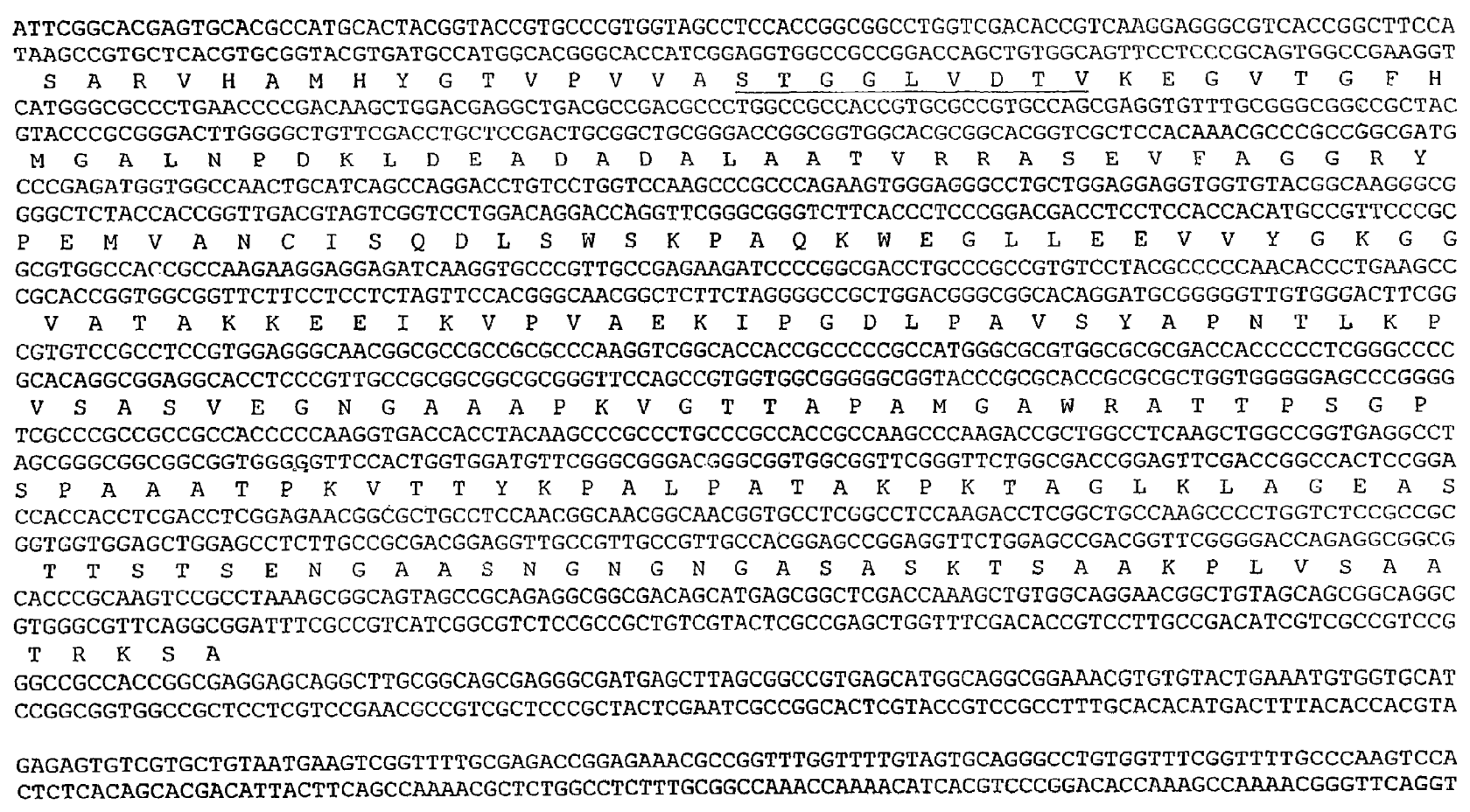

FIG. 1: cDNA coding for the carboxy terminal part of the GBSSI of *Chlamydomonas reinhardtii* (SEQ ID NOS 10–12 respectively in order of appearance).

FIG. 2: cDNA coding for the GBSSI of *Chlamydomonas reinhardtii*, and peptide sequence of the GBSSI of *Chlamydomonas reinhardtii* (SEQ ID NOS 1, 3 and 15, respectively in order of appearance).

The present invention relates to any recombinant nucleotide sequence characterized in that it comprises, in the direction 5'→3', a nucleotide sequence coding for an adenosine diphosphate glucose α-1,4-glucan α-4-glucosyltransferase or starch synthase (EC 2.4.1.21), or for a protein derived from this enzyme, especially by suppression, addition or substitution of one or more amino acids, the said starch synthase or derived protein having the property of migrating to the sites of biosynthesis of starch granules in plant cells and of attaching to the starch granules, the said nucleotide sequence coding for the enzyme or aforementioned protein being positioned upstream of a nucleotide sequence coding for a peptide or polypeptide of interest.

By starch synthase we mean, in the foregoing and hereinafter, any protein having the property of migrating to the sites of biosynthesis of starch granules in plant cells and of attaching to the starch granules, whether or not this starch synthase has conserved its enzymatic activity within the fusion polypeptide, encoded by an aforementioned recombinant nucleotide sequence, between the said starch synthase and the said polypeptide of interest.

Preferably, the nucleotide sequence coding for a starch synthase, or for a derived protein as defined above, is selected from those coding for a starch synthase bound to the starch granule GBSS that occurs in particular in plants, algae or micro-algae, and even more advantageously for an isoform GBSSI, or for a protein derived from this GBSS, or GBSSI, as defined above.

The invention relates more particularly to any recombinant nucleotide sequence as defined above, characterized in that the nucleotide sequence coding for a starch synthase, and more particularly for a GBSS, and especially for a GBSSI, is such as is obtained by screening a cDNA library prepared from cells that are likely to contain this enzyme, especially from cells of plants, algae or micro-algae, by means of an antiserum containing antibodies specifically recognizing the said starch synthase coded by one or more cDNA in the library, when the said starch synthase is expressed by a suitable cloning vector, the said antiserum being obtained by immunization of an animal, such as a rabbit, with starch extracted from the aforementioned cells.

The invention relates more particularly to any recombinant nucleotide sequence as defined above, characterized in that the nucleotide sequence coding for a starch synthase, or for a derived protein, is selected from:

the nucleotide sequence of the cDNA of about 2900 to 3100 base pairs, and of which the 1696 base pairs of the 3' end are shown in FIG. 1, the said nucleotide sequence:

coding for the GBSSI of *Chlamydomonas reinhardtii* of about 640 to 680 amino acids, especially of about 660 amino acids, of which the amino terminal end corresponds to the following succession of amino acids: ALDIVMVAAEVAPGGKTGGLGDV (SEQ ID NO: 13), or ALDIVMVAAEVAPWSKTG-GLGDV (SEQ ID NO:14), and of which the carboxy terminal end corresponds to the succession of amino acids shown in FIG. 1, and being obtained by screening a cDNA library prepared from cells of *Chlamydomonas reinhardtii*, by means of an antiserum obtained by immunization of rabbits with the starch extracted from the aforementioned cells of *Chlamydomonas reinhardtii*, or a nucleotide fragment of the aforementioned cDNA, coding for a peptide fragment of the GBSSI of *Chlamydomonas reinhardtii*, the said peptide fragment comprising the whole of the amino terminal part of the said GBSSI, and being delimited at its carboxy terminal end by the amino acid located in one of the positions 25 to 238, or in one of the positions 118 to 238, of the amino acid sequence shown in FIG. 1, or a nucleotide sequence derived by degeneration of the genetic code of the nucleotide sequence of the aforementioned cDNA, or of an aforementioned nucleotide fragment of the latter, and coding for the aforementioned GBSSI of *Chlamydomonas* reinhardtii, or for an aforementioned peptide fragment of the latter, or a nucleotide sequence derived from an aforementioned nucleotide sequence or fragment, especially by substitution, suppression or addition of one or more nucleotides, and encoding a peptide sequence derived from the aforementioned GBSSI of *Chlamydomonas rein-*

*hardtii*, or derived from an aforementioned peptide fragment of the latter, and having the property of attaching to the starch granules, the said derived nucleotide sequence preferably having a homology of at least about 50%, and preferably of at least about 70%, with the aforementioned nucleotide sequence or fragment, or a nucleotide sequence capable of hybridization with one of the aforementioned nucleotide sequences or fragments, especially in the strict conditions of hybridization defined later, the property possessed by a starch synthase, or a fragment or a protein derived from the latter as defined above, of being able to attach to the starch granules, being measurable by the following technique: extraction of the proteins from the starch granules, for example according to the method described in detail below, and detection of the presence of the said starch synthase, or of a fragment or of a protein derived from the latter as defined above, especially by polyacrylamide gel electrophoresis according to the technique described in detail later.

The invention relates more particularly to any recombinant nucleotide sequence as defined above, characterized in that the aforementioned nucleotide sequence coding for a starch synthase, or for a derived protein, is more particularly selected from:

the nucleotide sequence of cDNA shown in FIG. 2, corresponding to SEQ ID NO:1 in the sequence list given later, the said nucleotide sequence coding for the GBSSI of *Chlamydomonas reinhardtii*, any fragment as defined above of the nucleotide sequence SEQ ID NO:1 shown in FIG. 2, and more particularly any sequence of which the nucleotide of the 5' end corresponds to that located in one of the positions 1 to 186 of SEQ ID NO:1, and of which the nucleotide of the 3' end corresponds to that located in one of the positions 1499 to 3117 of SEQ ID NO: 1, especially:

the sequence SEQ ID NO: 2 delimited by the nucleotides located in positions 15 to 2138 of SEQ ID NO:1, coding for the GBSSI of *Chlamydomonas reinhardtii* in the form of pre-protein of 708 amino acids (SEQ ID NO: 3) delimited by the amino acids located at positions 1 and 708 of the peptide sequence shown in FIG. 2, the sequence SEQ ID NO: 4 delimited by the nucleotides located at positions 186 to 2138 of SEQ ID NO: 1, coding for the GBSSI of *Chlamydomonas reinhardtii* in the form of a mature protein of 651 amino acids (SEQ ID NO: 5) delimited by the amino acids located at positions 58 and 708 of the peptide sequence shown in FIG. 2, the sequence SEQ ID NO: 6 delimited by the nucleotides located at positions 186 to 1499 of SEQ ID NO: 1, coding for a fragment of 438 amino acids (SEQ ID NO: 7) delimited by the amino acids located at positions 58 and 495 of the peptide sequence of the GBSSI of *Chlamydomonas reinhardtii* shown in FIG. 2, the sequence SEQ ID NO: 8 delimited by the nucleotides located at positions 186 to 1778 of SEQ ID NO:1, coding for a fragment of 531 amino acids (SEQ ID NO: 9) delimited by the amino acids located at positions 58 and 588 of the peptide sequence of the GBSSI of *Chlamydomonas reinhardtii* shown in FIG. 2, or a nucleotide sequence derived by degeneration of the genetic code of the aforementioned nucleotide sequences, and coding for the aforementioned GBSSI of *Chlamydomonas reinhardtii*, or for an aforementioned peptide fragment of the latter, or a nucleotide sequence derived from an aforementioned nucleotide sequence or fragment, especially by substitution, suppression or addition of one or more nucleotides, and encoding a peptide sequence derived from the aforementioned GBSSI of *Chlamydomonas reinhardtii*, or derived from an aforementioned peptide fragment of the latter, and having the property of attaching to the starch granules, the said derived nucleotide sequence preferably having a homology of at least about 50%, and preferably of at least about 70%, with the aforementioned nucleotide sequence or fragment, or a nucleotide sequence capable of hybridizing with one of the aforementioned nucleotide sequences or fragments, especially in the strict conditions of hybridization defined above.

The invention relates more particularly to any recombinant nucleotide sequence as defined above, characterized in that the nucleotide sequence coding for a peptide or polypeptide of interest is selected from those encoding biologically active peptides, especially peptides of therapeutic interest or that can be used in the agricultural and food industry.

The invention also relates to any recombinant nucleotide sequence as defined above, characterized in that the nucleotide sequence coding for a peptide or polypeptide of interest is selected from those encoding enzymes that are able to transform starch, such as the enzymes that interact with the α-glucans including various hydrolases, phosphorylases, α-1,4 glucanotransferases, branching enzymes, amylases, and especially the heat-resistant hydrolases obtained from extremophiles such as the archaebacteria that are active at temperatures above 40° C.

The invention also relates to any recombinant nucleotide sequence as defined above, characterized in that it comprises a nucleotide sequence coding for a cleavage site, the said nucleotide sequence being positioned between the nucleotide sequence coding for a starch synthase, or a protein derived from the latter, and the nucleotide sequence encoding the polypeptide of interest.

As an illustration, the nucleotide sequence coding for a cleavage site is selected from the sequences coding for a peptide sequence of the aspartyl-proline type, which is very unstable at acid pH, or coding for a small peptide sequence recognized specifically by a protease, such as trypsin, chymotrypsin, pepsin, collagenase, thrombin, alasubtilisin, or recognized by chemical compounds such as cyanogen bromide.

The invention also relates to any recombinant nucleotide sequence as defined above, characterized in that it comprises a promoter located upstream of the nucleotide sequence coding for a starch synthase, or a protein derived from the latter, as well as a sequence coding for transcription termination signals located downstream of the nucleotide sequence encoding the polypeptide of interest.

Among the transcription promoters suitable for use within the scope of the present invention, we may mention:

for prokaryotic promoters, the Lac or T7 promoters, for the eukaryotic promoters of higher plant type, the promoter 35S CaMV, or any type of promoter of plant origin, in the case of the transformation of micro-algae, the promoter used can be that of the ARG7 gene encoding arginosuccinate lyase or the promoter of the NIT1 gene encoding nitrate reductase.

The invention also relates to any recombinant vector, especially of the plasmid, cosmid or phage type, characterized in that it contains a recombinant nucleotide sequence according to the invention as defined above, inserted in a site that is non-essential for its replication.

The invention also relates to any cellular host, transformed by a recombinant vector as defined above, especially any bacterium such as *Agrobacterium tumefaciens*, and comprising at least one recombinant nucleotide sequence according to the invention.

The invention also relates to any fusion polypeptide characterized in that it comprises:

in the N-terminal position, a starch synthase, or a protein derived from that enzyme, especially by suppression, addition or substitution of one or more amino acids, the said starch synthase or derived protein having the property of migrating to the sites of biosynthesis of the starch granules in plant cells and of attaching to the starch granules, and, in the C-terminal position, a peptide or polypeptide of interest, the C-terminal part of the amino acid sequence of the starch synthase, or of the derived protein, being thus bound to the N-terminal part of the peptide sequence of interest, the said fusion polypeptide being encoded by a recombinant nucleotide sequence as defined above according to the invention.

The invention relates more particularly to any fusion polypeptide as defined above, characterized in that it includes, in the N-terminal position, a GBSS that occurs in particular in plants, algae or micro-algae, and more particularly an isoform GBSSI, or a protein derived from the latter as defined above.

The invention relates more particularly to any fusion polypeptide as defined above, characterized in that the starch synthase is selected from:

the GBSSI of *Chlamydomonas reinhardtii* of about 640 to 680 amino acids, of which the amino terminal end corresponds to the following succession of amino acids: ALDIVMVAAEVAPGGKTGGLGDV (SEQ ID NO:13), or ALDIVMVAAEVAPWSKTGGLGDV (SEQ ID NO:14), and the carboxy terminal end corresponds to the succession of amino acids shown in FIG. 1, the said GBSSI being encoded by the nucleotide sequence obtained by screening a cDNA library prepared from cells of *Chlamydomonas reinhardtii*, by means of an antiserum obtained by immunization of rabbits with the starch extracted from the aforementioned cells of *Chlamydomonas reinhardtii*, or a peptide fragment of the GBSSI of *Chlamydomonas reinhardtii*, the said peptide fragment comprising the whole of the amino terminal part of the said GBSSI, and being delimited at its carboxy terminal end by the amino acid located in one of the positions 25 to 238, or in one of the positions 118 to 238, of the amino acid sequence shown in FIG. 1, or a peptide sequence derived from an aforementioned peptide sequence or fragment, especially by substitution, suppression or addition of one or more amino acids, and having the property of attaching to the starch granules, the said derived peptide sequence preferably having a homology of at least about 60%, and advantageously of at least about 80%, with the aforementioned peptide sequence or fragment, the property possessed by the GBSSI of *Chlamydomonas reinhardtii*, or a fragment or a protein derived from the latter as defined above, of being able to attach to the starch granules, being measurable by the technique described above.

The invention relates more particularly to any fusion polypeptide as defined above, characterized in that the starch synthase defined above is selected more particularly from:

the peptide sequence SEQ ID NO: 3 delimited by the amino acids located at positions 1 to 708 in FIG. 2, corresponding to the GBSSI of *Chlamydomonas reinhardtii* in the form of a pre-protein of 708 amino acids, any fragment as defined above from the peptide sequence SEQ ID NO: 3 shown in FIG. 2, and more particularly any sequence of which the amino acid of the amino terminal end corresponds to that located in one of the positions 1 to 58 of SEQ ID NO: 3, and of which the amino acid of the carboxy terminal end corresponds to that located in one of the positions 495 to 708 of SEQ ID NO: 3, especially:

the sequence SEQ ID NO: 5 delimited by the amino acids located at positions 58 to 708 of SEQ ID NO: 3, corresponding to the GBSSI of *Chlamydomonas reinhardtii* in the form of a mature protein of 651 amino acids, the sequence SEQ ID NO: 7 delimited by the amino acids located at positions 58 to 495 of SEQ ID NO: 3, corresponding to a fragment of 438 amino acids of the peptide sequence of the GBSSI of *Chlamydomonas reinhardtii* shown in FIG. 2, the sequence SEQ ID NO: 9 delimited by the amino acids located at positions 58 to 588 of SEQ ID NO: 3, corresponding to a fragment of 531 amino acids of the peptide sequence of the GBSSI of *Chlamydomonas reinhardtii* shown in FIG. 2, or a peptide sequence derived from an aforementioned peptide sequence or fragment, especially by substitution, suppression or addition of one or more amino acids, and having the property of attaching to the starch granules, the said derived peptide sequence preferably having a homology of at least about 60%, and advantageously of at least about 80%, with the aforementioned peptide sequence or fragment, the property possessed by the GBSSI of *Chlamydomonas reinhardtii*, or a fragment or a protein derived from the latter as defined above, of being able to attach to the starch granules, being measurable by the technique described above.

The invention relates more particularly to any fusion polypeptide as defined above, characterized in that the polypeptide of interest is selected from the biologically active peptides, especially the peptides of therapeutic interest or that can be used in the agricultural and food industry.

The invention also relates to any fusion polypeptide as defined above, characterized in that the polypeptide of interest is selected from the enzymes that are able to transform starch, such as the enzymes that interact with the α-glucans, including various hydrolases, phosphorylases, α-1,4-glucanotransferases, branching enzymes, amylases, and especially the heat-resistant hydrolases obtained from extremophiles such as the archaebacteria that are active at temperatures above 40° C.

The invention also relates to any fusion polypeptide as defined above, characterized in that it contains a cleavage site, as described above, positioned between on the one hand the starch synthase or a protein derived from the latter, and on the other hand the polypeptide of interest.

The invention also relates to genetically transformed plant cells, containing one or more recombinant nucleotide sequences as described above, integrated in their genome or maintained in a stable manner in their cytoplasm, the said plant cells being selected from the cells of plants, algae or micro-algae, capable of producing starch.

The invention also relates to transgenic plant cells as described above containing one or more fusion polypeptides defined above within the starch granules contained in the said plant cells.

The invention relates more particularly to the aforementioned transgenic plant cells, transformed with a recombinant nucleotide sequence containing the nucleotide sequence of cDNA of about 2900 to 3100 base pairs, and of which the 1696 base pairs of the 3' end are shown in FIG. 1, the said nucleotide sequence coding for the GBSSI of Chlamydomonas reinhardtii described above, or containing a fragment or a derived sequence as described above from the aforementioned cDNA.

The invention relates even more particularly to the aforementioned transgenic plant cells, transformed with:

the cDNA nucleotide sequence shown in FIG. 2, the said nucleotide sequence coding for the GBSSI of Chlamydomonas reinhardtii, any fragment as defined above of the nucleotide sequence shown in FIG. 2, or a derived nucleotide sequence, as defined above, from the aforementioned nucleotide sequences, or a nucleotide sequence capable of hybridization with one of the aforementioned nucleotide sequences or fragments, especially in the strict conditions of hybridization defined above.

The invention also relates to genetically transformed plants, algae or micro-algae, or parts, especially flowers, fruits, leaves, stems, roots, seeds, or fragments of these plants, algae or micro-algae, containing at least one recombinant nucleotide sequence as defined above integrated in the genome or maintained in a stable manner in the cytoplasm of the cells of which they are composed.

The invention also relates to genetically transformed plants, algae or micro-algae, or parts, or fragments of these plants, algae or micro-algae, as defined above, containing one or more fusion polypeptides as described above within the starch granules contained in the plant cells of which they are composed.

Among the plants, algae or micro-algae transformed within the scope of the present invention, we may mainly mention wheat, maize, potato, rice, barley, amaranth, algae of the genus Chlamydomonas, especially Chlamydomonas reinhardtii, algae of the genus Chlorella, especially Chlorella vulgaris, or single-celled algae of the genus Dunaliella (as described in the work "Dunaliella: Physiology, Biochemistry, and Biotechnology (1992), Mordhay Avron and Ami Ben-Amotz Publishers, CRC Press Inc., Boca Raton, Fla., USA").

The invention relates more particularly to the aforementioned transgenic plants, algae or micro-algae, transformed with a recombinant nucleotide sequence containing the cDNA nucleotide sequence of about 2900 to 3100 base pairs and of which the 1696 base pairs of the 3' end are shown in FIG. 1, the said nucleotide sequence coding for the GBSSI of Chlamydomonas reinhardtii described above, or containing a fragment or a derived sequence such as are described above of the aforementioned cDNA.

The invention relates even more particularly to the aforementioned transgenic plants, algae or micro-algae, transformed with:

the cDNA nucleotide sequence shown in FIG. 2, the said nucleotide sequence coding for the GBSSI of Chlamydomonas reinhardtii, any fragment as defined above of the nucleotide sequence shown in FIG. 2, or a derived nucleotide sequence, as defined above, of the aforementioned nucleotide sequences, or a nucleotide sequence capable of hybridizing with one of the aforementioned nucleotide sequences or fragments, especially in the strict conditions of hybridization defined above.

The invention also relates to starch granules characterized in that they include one or more fusion polypeptides defined above, the said starch granules being further designated by the expression "transformed starch granules" or "glucosomes".

The invention relates more particularly to the aforementioned starch granules comprising a fusion polypeptide defined above, the said fusion polypeptide containing the GBSSI of Chiamydomonas reinhardtii of about 640 to 680 amino acids described above, the amino terminal end of which corresponds to the following succession of amino acids: ALDIVMVAAEVAPGGKTGGLGDV (SEQ ID NO:113, or ALDIVMVAAEVAPWSKTGGLGDV (SEQ ID NO: 14), and the carboxy terminal end corresponds to the succession of amino acids shown in FIG. 1, or a fragment or a derived polypeptide such as are described above of the GBSSI of Chlamydomonas reinhardtii.

The invention relates more particularly to the aforementioned starch granules comprising a fusion polypeptide defined above, the said fusion polypeptide containing the sequence delimited by the amino acids located at positions 1 to 708 in FIG. 2 (SEQ ID NO:3), coding for the GBSSI of Chiamydomonas reinhardtii in the form of a pre-protein of 708 amino acids, or any fragment as defined above of the peptide sequence shown in FIG. 2, especially any sequence in which the amino acid of the amino terminal end corresponds to that located in one of the positions 1 to 58 in FIG. 2 and SEQ ID NO:3, and in which the amino acid of the carboxy terminal end corresponds to that located in one of the positions 495 to 708 in FIG. 2 and SEQ ID NO:3, such as the fragments mentioned above.

Advantageously, the aforementioned starch granules are characterized in that they have a diameter between about 0.1 $\mu$m and several tens of $\mu$m, and in that the proportion by weight of the fusion polypeptides in these granules is between about 0.1% and 1%.

The invention also relates to any pharmaceutical composition characterized in that it includes transformed starch granules as defined above, if necessary in combination with a physiologically acceptable vehicle, the said granules containing one or more fusion polypeptides as defined above, the peptide of interest in the said fusion polypeptides possessing a defined therapeutic effect.

Advantageously the aforementioned pharmaceutical compositions of the invention are in a form that can be administered parenterally, especially intravenously, or in a form that can be administered orally.

Preferably, the aforementioned pharmaceutical compositions that can be administered parenterally are characterized in that the diameter of the starch granules is between about 0.1 $\mu$m and several $\mu$m, especially between about 0.1 $\mu$m and 10 μm, and in that the proportion by weight of the fusion polypeptides in these granules is between about 0.1% and 1%.

Starch granules as described above, with small diameters between about 0.1 μm and about 10 μm, in which the proportion by weight of fusion polypeptides is between about 0.1% and 1%, are obtained advantageously:

- from plants or cells of plants transformed within the scope of the present invention and selected for their property of producing the aforementioned starch granules naturally, the said plants being selected in particular from rice and amaranth,
- or from parts of transformed plants within the scope of the present invention, the said parts of these plants producing the aforementioned starch granules naturally, such as the leaves of the plants,
- or from plants or cells of plants transformed within the scope of the present invention, these plants being selected from plants that have mutations such that they produce starch granules of small diameters as mentioned above, especially from the mutant plants described in Buléon A. et al., 1998,
- or from plants or cells of plants transformed within the scope of the present invention, these plants being selected from the plants transformed with the aid of antisense nucleotide sequences of all or part of the gene coding for ADP-glucose pyrophosphorylase required for the synthesis of ADP-glucose in plant cells, and especially from the transformed plants described in the article by Müller-Röber B. et al., 1992.

Advantageously, in the case of pharmaceutical compositions mentioned above that can be administered parenterally, the starch granules are preferably selected from those of amorphous structure in the case when we wish to obtain rapid release of the fusion polypeptide that they contain in the patient's blood, or conversely, from those of crystalline structure when we wish to release the fusion polypeptide progressively in the blood.

By way of illustration, amorphous starch granules can be obtained from seeds transformed according to the invention at the germination stage, or from specific mutant plants such as described by Shannon J. and Garwood D., 1984, especially from the mutant cultivars such as "amylose extender" of maize or indeed all mutant cultivars of plants, algae or micro-algae whose starch is amylose-enriched.

The starch granules according to the invention of crystalline structure, advantageously have about 30 to 35% of crystals, and can be obtained from seeds of plants, especially of cereals, that have just been harvested and at maturity, or from mutant plants such as described by Shannon J. and Garwood D., 1984, especially from the mutant cultivars such as "waxy" of maize or indeed all the mutant cultivars of plants, algae or micro-algae whose starch is devoid of amylose.

The invention also relates to any pharmaceutical composition characterized in that it includes one or more fusion polypeptides as defined above, if necessary in combination with a physiologically acceptable vehicle, the peptide of interest in the said fusion polypeptides possessing a defined therapeutic effect.

The invention also relates to any food composition as described above, characterized in that it contains transformed starch granules as defined above, the said granules containing one or more fusion polypeptides as defined above, the peptide of interest in the said fusion polypeptides being usable in the food-processing field.

The invention also relates to any food composition as described above, characterized in that it contains one or more fusion polypeptides as defined above, the peptide of interest in the said fusion polypeptides being usable in the food-processing field.

The present invention also relates to any method of obtaining plant cells (from plants, algae or micro-algae), and, if necessary, from whole plants, algae or micro-algae, transformed by at least one nucleotide sequence as defined above, characterized in that it comprises:

- the transformation of plant cells, in such a way as to integrate in the genome of these cells, or maintain in a stable manner in their cytoplasm, one or more recombinant nucleotide sequences according to the invention, and cultivation of these transformed cells in vitro,
- if necessary, the production of transformed plants from the aforementioned transformed cells.

According to one embodiment of the aforementioned method of the invention, the transformation of plant cells can be carried out by transfer of the recombinant nucleotide sequence of the invention in the protoplasts, especially after incubation of the latter in a solution of polyethylene glycol (PEG) in the presence of divalent cations ($Ca^{2+}$) according to the method described in the article by Krens et al., 1982.

Transformation of the plant cells can also be carried out by electroporation especially according to the method described in the article by Fromm et al., 1986.

Transformation of the plant cells can also be carried out using a gene gun, by means of which metal particles coated with recombinant nucleotide sequences according to the invention are propelled at high velocity, thus delivering genes to the interior of the cell nucleus, especially in accordance with the technique described in the article by Sanford, 1988.

Another method of transformation of plant cells is the method of cytoplasmic or nuclear micro-injection as described in the article by De La Penna et al., 1987.

According to a particularly preferred embodiment of the aforementioned method of the invention, the plant cells are transformed by putting the latter in the presence of a cellular host transformed by a vector according to the invention, as described above, the said cellular host being able to infect the said plant cells making it possible to integrate in the genome or maintain in a stable manner in the cytoplasm of the latter, recombinant nucleotide sequences of the invention initially contained in the genome of the aforementioned vector.

Advantageously, the aforementioned cellular host employed is *Agrobacterium tumefaciens*, especially according to the methods described in the articles of Bevan, 1984 and of An et al., 1986, or *Agrobacterium rhizogenes*, especially according to the method described in the article by Jouanin et al., 1987.

Among the plant cells capable of being transformed within the scope of the present invention, we may mention mainly the cells of wheat, maize, potato, rice, barley, amaranth, *Chlamydomonas reinhardtii, Chlorella vulgaris*.

According to one embodiment of the aforementioned method of the invention, the plant cells transformed according to the invention are cultivated in vitro, especially in bioreactors according to the method described in the article by Brodelius, 1988, in a liquid medium, or according to the method described in the article by Brodelius et al., 1979, in immobilized form, or according to the method described in the article by Deno et al., 1987, by culture of roots transformed in vitro.

According to a preferred embodiment of the aforementioned method of the invention, the transformation of plant cells is followed by a stage of obtaining transformed plants by culturing the said transformed cells in a suitable medium, and, if necessary, fertilization and recovery of the seeds of the plants obtained in the preceding stage, and cultivation of these seeds to obtain plants of the next generation.

The seeds transformed according to the invention are harvested from the aforementioned transformed plants, these plants being either those of the T0 generation, i.e. those obtained from culture of transformed cells of the invention on a suitable medium, or advantageously those of the next generations (T1, T2 etc.) obtained by self-fertilization of the plants of the preceding generation and in which the recombinant nucleotide sequences of the invention are reproduced in accordance with Mendel's laws, or the laws of extrachromosomal inheritance.

The invention also relates to a method of preparation of transformed starch granules as described above, characterized in that it comprises a stage of extraction of the starch granules from transformed plant cells or from plants, or from parts, especially flowers, fruits, leaves, stems, roots, or from fragments of these plants, transformed as mentioned above, especially by sedimentation in the conditions described later.

Preferably, the starch granules according to the invention are those obtained by extraction from transformed plants, algae or micro-algae, described above, or from parts, or fragments of these plants, algae or micro-algae, defined above, especially by sedimentation in the conditions described later.

The transformed plants used for recovering the starch granules are those of the T0 generation, or advantageously those of the next generations (T1, T2 etc.) mentioned above.

The invention also relates to a method of preparation of fusion polypeptides as defined above, characterized in that it comprises a stage of recovery, and if necessary of purification, of the fusion polypeptides from the aforementioned transformed starch granules especially in the conditions described later.

The invention also relates to a method of preparation of a peptide of interest, characterized in that it comprises the implementation of a method as described above for obtaining plant cells or transformed plants according to the invention, the said method being carried out by transformation of plant cells with the aforementioned nucleotide sequences coding for a fusion polypeptide containing a cleavage site as described above, and includes an additional stage of cleavage of the said fusion polypeptide, by means of a suitable reagent, then, if necessary, a stage of purification of the polypeptide of interest.

The invention also relates to a method of biotransformation of starch granules, characterized in that it comprises the following stages:
transformation of plant cells as defined above with the aid of host cells described above containing one or more nucleotide sequences coding for enzymes capable of transforming starch as mentioned above,
production of plants, algae or micro-algae transformed in such a way that their genome contains one or more nucleotide sequences described above, by culture in vitro of the aforementioned transformed plant cells,
if necessary, fertilization and recovery of the seeds of the plants obtained in the preceding stage, and culture of these seeds to obtain plants of the next generation,
extraction of starch granules from the aforementioned transformed plants, algae or micro-algae, or from parts, especially flowers, fruits, leaves, stems, roots, or from fragments of these plants, algae or micro-algae, especially by sedimentation in the conditions described later,
if necessary, heating of the said starch granules to a temperature at which the peptide of interest of the aforementioned fusion polypeptide is capable of being active.

Preferably, when the methods described above are carried out by transformation of plant cells, the latter are transformed with the aforementioned recombinant sequences containing the cDNA nucleotide sequence of about 2900 to 3100 base pairs, and of which the 1696 base pairs of the 3' end are shown in FIG. 1, the said nucleotide sequence coding for the GBSSI of *Chlamydomonas reinhardtii* described above, and more particularly with recombinant sequences as mentioned above containing the nucleotide sequence shown in FIG. 2, or containing a fragment or a derived sequence as described above of the nucleotide sequence shown in FIG. 2. The use of these recombinant sequences containing the nucleotide sequence coding for the GBSSI of *Chlamydomonas* reinhardtii described above makes it possible advantageously to avoid the development of effects of co-suppression in the transformed plants thus obtained.

The invention also relates to a method of preparation of antibodies specifically recognizing a starch synthase bound to the starch granule, of a given plant, algae or micro-algae, by immunization of an animal, especially of a rabbit, with the starch obtained from the said plant, algae or micro-algae.

Therefore, the invention relates more particularly to a method of preparation of antibodies specifically recognizing the GBSSI, of a given plant, algae or micro-algae, by immunization of an animal, especially of a rabbit, with the starch obtained from the said plant, algae or micro-algae.

The invention also relates more particularly to a method of preparation of antibodies specifically recognizing an isoform of GBSS other than GBSSI, from a given plant, algae or micro-algae, by immunization of an animal, especially a rabbit, with the starch obtained from the said plant, algae or micro-algae having a mutation such that the expression of the GBSSI is suppressed, for example a mutation selected from the following: sta2-29::ARG7 in *Chlamydomonas reinhardtii* (described by Delrue et al., 1992, mentioned above), amf in the potato (described by Hovenkamp-Hermelink et al., 1987, mentioned above), wx in maize, rice and wheat (described by Tsai; 1974, mentioned above), lam in the pea (described by Denyer et al., 1995, mentioned above).

The invention also relates to a method of obtaining starch synthase, such as GBSS, and more particularly for the isoform GBSSI, from a given plant, algae or micro-algae, by screening a cDNA library prepared from cells of the said given plant, algae or micro-algae, capable of containing this enzyme, using an antiserum containing antibodies specifically recognizing the said enzyme encoded by one or more cDNA's from the library, when the said enzyme is expressed by a suitable cloning vector, the said antiserum being obtained according to the method mentioned above.

The invention also relates to the nucleotide sequences coding for a starch synthase or for a derived protein, selected from:
the cDNA nucleotide sequence shown in FIG. 2, corresponding to SEQ ID NO: 1 in the sequence list given later, the said nucleotide sequence coding for the GBSSI of *Chlamydomonas reinhardtii*,
any fragment as defined above of the nucleotide sequence SEQ ID NO: 1 shown in FIG. 2, and more particularly any sequence whose nucleotide of the 5' end corresponds to that located in one of the positions 1 to 186 of SEQ ID NO:1, and whose nucleotide of the 3' end corresponds to that located in one of the positions 1499 to 3117 of SEQ ID NO: 1, especially:

the sequence SEQ ID NO: 2 delimited by the nucleotides located at positions 15 to 2138 of SEQ ID NO: 1, coding for the GBSSI of Chlamydomonas reinhardtii in the form of pre-protein of 708 amino acids (SEQ ID NO: 3) delimited by the amino acids located at positions 1 and 708 of the peptide sequence shown in FIG. 2, the sequence SEQ ID NO: 4 delimited by the nucleotides located at positions 186 to 2138 of SEQ ID NO:1, coding for the GBSSI of Chlamydomonas reinhardtii in the form of mature protein of 651 amino acids SEQ ID NO: 5) delimited by the amino acids located at positions 58 and 708 of the peptide sequence shown in FIG. 2, the sequence SEQ ID NO: 6 delimited by the nucleotides located at positions 186 to 1499 of SEQ ID NO: 1, coding for a fragment of 438 amino acids (SEQ ID NO: 7) delimited by the amino acids located at positions 58 and 495 of the peptide sequence of the GBSSI of Chlamydomonas reinhardtii shown in FIG. 2, the sequence SEQ ID NO: 8 delimited by the nucleotides located at positions 186 to 1778 of SEQ ID NO: 1, coding for a fragment of 531 amino acids (SEQ ID NO: 9) delimited by the amino acids located at positions 58 and 588 of the peptide sequence of the GBSSI of Chlamydomonas reinhardtii shown in FIG. 2, or a nucleotide sequence derived by degeneration of the genetic code of the aforementioned nucleotide sequences, and coding for the aforementioned GBSSI of Chlamydomonas reinhardtii, or for an aforementioned peptide fragment of the latter, or a nucleotide sequence derived from an aforementioned nucleotide sequence or fragment, especially by the substitution, suppression or addition of one or more nucleotides, and encoding a peptide sequence derived from the aforementioned GBSSI of Chlamydomonas reinhardtii, or derived from an aforementioned peptide fragment of the latter, and having the property of attaching to the starch granules, the said derived nucleotide sequence preferably having a homology of at least about 50%, and preferably of at least about 70%, with the aforementioned nucleotide sequence or fragment, or a nucleotide sequence capable of hybridizing with one of the aforementioned nucleotide sequences or fragments, especially in the strict conditions of hybridization defined above.

The invention also relates to the polypeptides selected from:

the peptide sequence SEQ ID NO: 3 delimited by the amino acids located at positions 1 to 708 in FIG. 2, corresponding to the GBSSI of Chlamydomonas reinhardtii in the form of pre-protein of 708 amino acids, any fragment as defined above of the peptide sequence SEQ ID NO: 3 shown in FIG. 2, and more particularly any sequence whose amino acid of the amino terminal end corresponds to that located in one of the positions 1 to 58 of SEQ ID NO: 3, and whose amino acid of the carboxy terminal end corresponds to that located in one of the positions 495 to 708 of SEQ ID NO: 3, especially:

the sequence SEQ ID NO: 5 delimited by the amino acids located at positions 58 to 708 of SEQ ID NO: 3, corresponding to the GBSSI of Chlamydomonas reinhardtii in the form of mature protein of 651 amino acids, the sequence SEQ ID NO: 7 delimited by the amino acids located at positions 58 to 495 of SEQ ID NO: 3, corresponding to a fragment of 438 amino acids of the peptide sequence of the GBSSI of Chlamydomonas reinhardtii shown in FIG. 2, the sequence SEQ ID NO: 9 delimited by the amino acids located at positions 58 to 588 of SEQ ID NO: 3, corresponding to a fragment of 531 amino acids of the peptide sequence of the GBSSI of Chlamydomonas reinhardtii shown in FIG. 2, or a peptide sequence derived from an aforementioned sequence or peptide fragment, especially by substitution, suppression or addition of one or more amino acids, and having the property of attaching to the starch granules, the said derived peptide sequence preferably having a homology of at least about 60%, advantageously at least about 80%, with the aforementioned peptide sequence or fragment, the property possessed by the GBSSI of Chlamydomonas reinhardtii, or a fragment or a protein derived from the latter as defined above, of being able to attach to the starch granules, being measurable by the method described above.

The invention also relates to polyclonal or monoclonal antibodies, directed against the aforementioned polypeptides.

The invention will be further illustrated by means of the following detailed description of cloning of the gene coding for the GBSSI of Chlamydomonas reinhardtii, and obtaining transformed starch granules containing a fusion polypeptide with the said GBSSI, as well as by means of FIG. 1 showing the nucleotide sequence and the protein sequence deduced from the cDNA insert of the CD142 clone coding for the GBSSI of Chlamydomonas reinhardtii (the underlined sequence corresponds to one of the three regions that are highly conserved across all the starch and glycogen synthases and is probably involved in fixation of the ADP-glucose substrate).

I) Cloning of the cDNA (Complementary DNA) and gDNA (Genomic DNA) Sequences Corresponding to the Structural Gene of the GBSSI of Chlamydomonas reinhardtii.

A) Cloning of the cDNA

The strategy developed for cloning the cDNA corresponding to the structural gene of the GBSSI of Chlamydomonas reinhardtii makes use of screening of an expression library using a polyclonal antiserum. The antiserum is able to recognize a polypeptide sequence encoded by a cDNA expressed from a suitable cloning vector.

a) Production of the Antiserum

In order to produce an antiserum capable of specifically recognizing the GBSSI of C. reinhardtii, the starch obtained from the wild strain (137C) was injected on three occasions into an albino New Zealand hybrid rabbit. In a similar experiment, the residual starch from a double mutant strain at loci STA2 and STA3 (IJ2) was injected in the rabbit in the same conditions.

Detailed Protocols:

Genotypes of the strains of C. reinhardtii:

137C: mt-nit1 nit2

IJ2: mt-nit1 nit2 sta2-29::ARG7 sta3-1

The 137C strain is the reference strain for all the studies of starch metabolism carried out in C. reinhardtii. The IJ2 strain was fully described by Maddelein et al. in 1994. In this double mutant strain at the STA2 and STA3 loci, the GBSSI and SSII activities are absent simultaneously. The mutation at the STA2 locus was generated by gene interruption by means of the pARG7 plasmid (Maddelein et al., 1994) and leads to complete disappearance of the GBSSI from the starch granule, whereas the mutant allele of the STA3 gene was generated by mutagenesis by X-rays (Fontaine et al., 1993).

Conditions for culture, extraction and purification of the starch: the cells were cultured for 3 days in the TAP medium with continuous illumination (3000 lux) from an inoculum of $5 \times 10^4$ cells/ml. The main culture is stopped when the cell concentration reaches about $2 \times 10^{-6}$ cells/ml.

Composition of the TAP medium (values for one liter of medium):

| | | | |
|---|---|---|---|
| NH$_4$Cl | 0.40 g | ZnSO$_4$.7H$_2$O | 22 mg |
| Tris | 2.40 g | H$_3$BO$_3$ | 11.4 mg |
| KH$_2$PO$_4$ | 0.32 g | MnCl$_2$.4H$_2$O | 5.1 mg |
| K$_2$HPO$_4$ | 1.47 g | FeSO$_4$.7H$_2$O | 4.2 mg |
| CaCl$_2$.2H$_2$O | 0.05 g | MoO$_3$ | 1.8 mg |
| MgSO$_4$.7H$_2$O | 0.30 g | CoCl$_2$.6H$_2$O | 1.6 mg |
| EDTA | 50 mg | CuO$_4$.5H$_2$O | 1.6 mg |

The pH of the medium is adjusted to 7 with glacial acetic acid

The TAP-N medium has the same base composition, but this medium differs from the first by the absence of nitrogen supplied in the form of ammonium chloride, which is replaced with sodium chloride at the same concentration; it is in these culture conditions that the cells accumulate a quantity of starch representing up to twenty times that of cells cultivated in TAP medium. In this case, culture is conducted for 5 days in continuous light starting from a culture inoculated at $5 \times 10^{-5}$ cells/ml.

The cells are then concentrated by centrifugation at $2-4 \times 10^{-8}$ cells/ml (Tris/acetate buffer pH 7.5 50 mM; EDTA 10 mM; DTT 2.5 mM) then subjected to the action of a French press at 10000 psi. The extract obtained at press discharge is centrifuged at 5000 g for 15 min at 4° C. The deposit containing the starch is resuspended in one volume of water, to which are added nine volumes of Percoll (Pharmacia, Uppsala, Sweden) before being centrifuged at 10000 g for 30 min at 4° C. The Percoll forms a density gradient during centrifugation. The starch, which has a high density (1.3 to 1.5), settles to the bottom of the tube whereas the lipids and other cell debris of low density form a "cap" at the surface of the Percoll gradient. The starch deposit is then rinsed three times with deionized water then stored at 4° C. after removing from it the last supernatant from rinsing.

Conditions for immunization of the rabbit, taking and preparation of the antiserum: the rabbit used in this experiment is an albino New Zealand hybrid rabbit. Three successive injections were made at intervals of three weeks with 20 mg of purified starch suspended in 500 µl of water. 500 µl of standard Freud adjuvant was added to this suspension. Blood samples were taken from the rabbit 3 weeks after the last injection. The serum is prepared by the single centrifugation of the blood after 24 hours of coagulation at 4° C. The antisera generated by the injections of the starches of the 137C and IJ2 strains are identified in the following by the designations "antiserum SA137C" and "antiserum SAIJ2" respectively.

b) Preparation and Screening of the cDNA Library

The cDNA library was produced from mRNA's purified from the wild strain of C. reinhardtii. The λ ZAP expression vector was used.

Detailed Protocols:

Preparation of the complete RNA's of C. reinhardtii: this method is an adaptation of the method used for extracting RNA's from the leaves of Arabidopsis thaliana. The cells of a culture of $1-2 \times 10^{-6}$ cells/ml are harvested by centrifugation at 3500 g for 15 min at 4° C. The cells are then divided into aliquots with a volume of about 200 µl. At this stage, the cells are frozen in liquid nitrogen and can be stored at −80° C. for several months. 400 µl of "Z6" buffer of the following composition is added to the 200 µl of frozen cells:

| | | |
|---|---|---|
| Buffer Z6: | MES/NaOH pH 7.0 | 20 mM |
| | EDTA | 20 mM |
| | Guanidine-HCl | 6 M |
| | β-Mercaptoethanol | 100 µM. |

The mixture is stirred very vigorously for several minutes, then 400 µl of phenol/chloroform/isoamyl alcohol mixture (25 v/24 v/1 v) is added and the mixture is stirred vigorously again for several minutes. The whole is centrifuged at 13000 g for 10 min at 4° C. After recovering and then estimating the volume of the supernatant, 1/20 volume of acetic acid at 1 M as well as 0.7 volume of 100% ethanol are added. The nucleic acids are given time to precipitate at −20° C. for at least 30 min. After centrifugation at 13000 g for 15 min at 4° C., the pellet is resuspended in 400 µl of 3 M sodium acetate pH 5.6 then centrifuged for 10 min at 13000 g at 4° C. The pellet is then rinsed twice with 70% ethanol, dried and finally dissolved in 50 µl of water treated with DEPC. The quantity of nucleic acids is determined in a spectrophotometer at 260 nm ($OD_{260}=1$ is equivalent to about 40 µg/ml of nucleic acids).

Construction of a cDNA library in the λ ZAP vector: the RNA's having a polyA tail (the mRNA's in particular) are isolated from the total RNA preparation using the kit "polyA Ttract mRNA isolation systems" marketed by Promega (Madison, Wis., USA). Synthesis of the cDNA's, ligation in the λ ZAP vector and packaging in the capsids are effected using the kit "cDNA synthesis kit, ZAP-cDNA synthesis kit and ZAP-cDNA gigapack II gold cloning kit" marketed by Stratagene (La Jolla, Calif., USA). The procedure followed corresponds to the instruction manual supplied with the kit.

Immunological screening of a cDNA library in an expression vector: screening of the cDNA expression library of λ ZAP from C. reinhardtii was carried out using the antiserum previously obtained (see above). About 100000 lysis plates are spread by the Top-agar technique on several Petri dishes containing bacterial growth medium and the adapted antibiotic. After incubation for 3 hours at 37° C., nitrocellulose filters (Protan BA 85, Schleicher & Schuell, Dassel, Germany), previously immersed in a solution of IPTG 10 mM and dried, are applied to the surface of the Top-agar. The dishes are incubated again for 3 hours at 37° C. before being stored at 4° C. for 30 min. The nitrocellulose filters are then carefully removed from the agar surface. The E. coli strain XL1-blue was used during screening of the λ ZAP library.

The protocol for filter development is then the same as that used in the Western Blot study (see the section dealing with Western Blot).

The positive lysis regions are subjected to two successive series of screening with the same antiserum in order to confirm their positive character, and also to purify them. When a lysis region is found to be positive at the end of three screenings, the sequence of the plasmid pBluescript SK+ containing the insert of interest is excised from the λ phage in vivo. It is the "ExAssist helper phage" that is used for cotransfection of the SOLR strain with the λ ZAP phage. In this way we obtain a phagemid that is used for infecting the strain XL1-Blue MRF' leading to restoration of the double-stranded plasmid pBluescript SK+ bearing the cDNA of interest.

Screening of this kind, conducted with the SA137C antiserum, led to the production of a single positive clone after three screenings. We designated this clone "CD142". The insert of the CD142 clone has a size of 1696 bp (see the sequence in FIG. 1).

c) Sequence Analysis of the Insert of the CD142 Clone

When the protein sequence libraries are interrogated with the sequence derived from the cDNA clone "CD142", the greatest similarities are obtained with the GBSSI of the higher plants. This first indication of the origin of this cDNA is reinforced by the presence of an extension of 119 amino acids (about 14 kDa) in the carboxy terminal position of the coding sequence, relative to the main GBSSI's of the higher plants. In fact, the molecular weight of the GBSSI of *C. reinhardtii*, determined by SDS-PAGE, is on average 10 to 15 kDa higher than that of the corresponding proteins in plants. The 119 amino acid extension might explain this difference in molecular weight between GBSSI's of different origins. Taken separately, this extension of the coding sequence does not share any similarity with other known types of polypeptide sequences.

The presence of the UAA stop codon in position 717 signals the start of a very long non-coding region of 946 bp. These noncoding regions in 3' terminal position, which frequently occur in the nuclear genes of Chlamydomonas, seem in particular to be intended to stabilize the messenger.

B) Cloning of gDNA

The gDNA relating to the CD142 clone was isolated after screening an indexed gDNA library in cosmids (Zhang et al., 1994). Constructed in a cosmid vector derived from c2RB, this gDNA library is contained in 120 96-well microtitration plates. Each well (apart from two, to facilitate orientation of the plate) contains a bacterial clone transporting a single cosmid. The whole library thus represents 11280 clones for which the average size of the inserts is approx. 38 kb. The nuclear genome of *C. reinhardtii* is therefore represented there statistically about four times.

Screening of this library with a probe corresponding to the CD142 clone led to the isolation of a genomic DNA clone designated 18B1. The insert present in this single cosmid was analysed in more detail. After restriction by NotI then hybridization with the CD142 probe, only a band of about 9 kb remains positive, indicating that all the information corresponding to the CD142 clone is present in this fragment. The genomic sequence corresponding to the CD142 clone is presented below.

Detailed Protocols:

Preparation of nylon filters for screening: the nylon filters (Hybond N, Amersham Buchler, Braunschweig, Germany) are carefully placed on a Petri dish containing a rich bacterial growth medium supplemented with the appropriate antibiotic (in the present case, ampicillin is used). Each *E. coli* clone contained in the library is then replicated directly on the nylon filter using a replicating apparatus and the dishes thus prepared are incubated overnight at 37° C. The filters are then removed from the agar surface and subjected to the following treatment:

(1) 2 min with a denaturing solution (NaOH 0.5 M; NaCl 1.5 M)

(2) 2 min with a neutralizing solution (Tris/HCl pH 7.0 0.5 M; NaCl 1.5 M)

(3) 2 min with a rinsing solution (buffer 2×SSC)

Finally the filters are incubated in a drying cabinet for 2 hours at 80° C.

Prehybridization and hybridization of the filters: prehybridization is carried out in the hybridization buffer at 42° C. for at least 4 hours. Hybridization is effected at 42° C. for a whole night in the presence of the $^{32}$P-labelled nucleotide probe. The membrane is washed at 60° C. in the washing solution, adjusted to the stringency that we wish to apply. The time and frequency of replacement of the washing baths vary depending on the stringency and the radioactivity levels detected on the membrane. In general, the baths are renewed every 10 min and washing begins with a washing buffer of low stringency and ends with a buffer of greater stringency. A Kodak X-OMAT AR film is finally exposed to the filters at −80° C. in order to detect the positive clones.

Composition of the Solutions and Buffers:

Buffer SSC×20: Dissolve 175.3 g of NaCl and 88.2 g of sodium citrate in 800 ml of water. Adjust the pH to 7.0 with a few drops of a 10 N solution of NaOH. Make up to 1 liter with water.

| Hybridization buffer: | |
| --- | --- |
| Formamide | 50% |
| Denhardt's | ×5 |
| SDS | 0.5% |
| Na phosphate buffer pH 7.0 | 50 mM |
| DNA of salmon sperm | 100 µg/ml |
| Bovine serum albumin | 0.5% |
| Denhardt's reagent × 100 | |
| (quantity for 500 ml in water): | |
| Ficoll 400 | 10 g |
| PolyVinylPyrrolidone 40 (PVP40) | 10 g |
| BSA | 10 g |
| Phosphate buffer pH 7.0 at 1 M (quantity for 100 ml of buffer): | |
| Na$_2$HPO$_4$ 1 M | 57.7 ml |
| NaH$_2$PO$_4$ 1 M | 42.3 ml |
| Washing buffers: | |
| low stringency: | SSC × 2; SDS 0.2% |
| medium stringency: | SSC × 1; SDS 0.5% |
| high stringency: | SSC × 0.5; SDS 0.5% |
| | SSC × 0.1; SDS 0.5% |

Preparation and labelling of a nucleotide probe with $^{32}$P: the fragment serving as nucleotide probe is generally inserted in the multiple cloning site of a bacterial plasmid. It is therefore first necessary to digest it with the appropriate restriction endonucleases then separate the fragment of interest from the rest of the plasmid by electrophoresis on 1% agarose gel buffered with TAE buffer×1. The band corresponding to the fragment of interest is then cut out of the gel and DNA extraction is effected with the kit "The GENECLEAN II Kit" marketed by BIO 101 Inc. (La Jolla, Calif., USA). The piece of agarose is firstly dissolved in a 6 M sodium iodide solution. On completion of solution, the DNA molecules are then captured with a silica matrix designated "Glassmilk". The DNA molecules, in the presence of the NaI chaotropic agent, are adsorbed specifically on the silica beads. After eliminating the salts and the dissolved agarose, the DNA molecules are eluted from the silica beads in the presence of sterile water.

Labelling of a nucleotide probe with $^{32}$P is accomplished using the "Random primed DNA labelling kit" from Boehringer (Mannheim, Germany). The principle is random priming of the elongation reaction by Klenow DNA polymerase using a mixture of hexanucleotides representing all the possible combinations of sequences. The radioactive element is incorporated starting from [α-$^{32}$P]-dCTP (3000 Ci/mmol) of which 50 µCi is used for each labelling reaction. The radiolabelled probe is finally added to the hybridization solution after denaturing at 95° C. for 4 min.

C) The STA2 Locus in C. reinhardtii Represents the Structural Gene of the GBSSI

The following analysis demonstrates formally that the STA2 gene of C. reinhardtii corresponds to the structural gene of the GBSSI and that the CD142 clone represents a cDNA that comes from this locus. In fact, restriction analyses of the genomic DNA digested by the BamHI endonuclease reveal a profound change of the restriction profile in the mutant BAFR1 strain at the STA2 locus generated by gene interruption (Delrue et al., 1992). The same change is also observed in the double mutant IJ2 strain at the STA2 and STA3 loci which Maddelein et al. (1994) generated by crossing the BAFR1 strain with a sta3-1 mutant strain.

Moreover, this change of the restriction profile in the meiotic progeny of the IJ2 strain fused with the "CS9" strain of C. smithii could be followed in the following crossing:

```
     CS9              X              IJ2
(C. smithii)                   (C. reinhardtii)

+/+                        sta2-29::ARG7/sta3-1

↓

+/+                25% sta2-29::ARG7/sta3-1    25%   progeny sta2-29::ARG7/+         25%   meiotic

/sta3-1            25%
```

352 segregants resulting from this crossing were purified, amplified and their starch accumulation phenotype was analysed. 54 meiotic recombinants underwent restriction analysis: 21 of genotype sta2-29::ARG7/+, 19 of genotype +/sta3-1 and 14 wild. With regard to the 21 segregants of genotype sta2-29::ARG7/+their restriction profile, obtained by digestion with BamHI and hybridized with the CD142 probe, still has the same change as the parental strain IJ2. We deduce from this that the STA2 gene and the CD142 probe are very strongly linked genetically. There is no longer any doubt as to the nature of the CD142 clone, which represents the structural gene of the GBSSI (the STA2 locus).

Detailed Protocols:

Carrying out the crossings: before carrying out the fusion of cells with opposite sexual polarities, it is necessary to put them in a state that is favourable to their fusion. Thus, the cells must first be differentiated into gametes before they are put in direct contact. Gametogenesis is induced in Chlamydomonas by subjecting the cells to a nitrogen deficit and in the presence of a strong light source (5000 lux). For this, fresh cells cultivated on rich agar medium (culture of less than 5 days) are suspended in 2 ml of TAP-N medium and left for at least 12 hours in strong light without agitation. The state of the cells is examined with an optical microscope before being brought into contact. After differentiation into gametes, the cells are smaller and in particular much more active than in the case of a non-deficient culture. Equivalent quantities of cells of each sexual polarity are mixed. Fusion is always carried out in strong light. After one hour of contact, cell fusions are already visible in the optical microscope. Analysis of the meiotic segregants will consist of depositing the products of cellular fusion on a rich medium at 4% agar. The dishes thus obtained are incubated in diffuse light for 15 hours then stored in total darkness for at least a week. This permits maturation of the zygotes and their "encystment" in the 4% agar. After this period of incubation in darkness, the dishes are returned to the light and the following stages are carried out as quickly as possible. In order to eliminate the greatest possible number of unfused vegetative cells, the surface of the agar is scraped very lightly with a razor blade. Observing with a binocular magnifier, a region containing about fifty zygotes is marked off and these are transferred to a fresh dish of rich medium at 1.5% agar. To be sure of complete disappearance of residual vegetative cells, the dish is subjected to chloroform vapours for 45 seconds to 1 minute (in contrast to other cells, zygotes can withstand this moderate time of exposure to chloroform vapours). The presence of light will irreversibly trigger the start of meiosis of the zygotes. During their germination (facilitated by the higher moisture content of the medium containing 1.5% agar) the zygotes will release four haploid daughter cells (a tetrad), which will grow by mitotic divisions and form colonies in the dish. Analysis of the meiosis products can be effected in two ways. The first consists of random investigation of at least 200 segregants resulting from the crossing. After purification of the segregants, the characters of the latter can be studied by replication on different selective media.

Techniques of extraction of genomic DNA: the protocol adopted for extraction of total DNA is that described by Rochaix et al. (1991); here are the details:

(1) Centrifuge 10 ml of cell culture to about 3–5×10$^6$ cells/ml for 10 min at 3500 g in a 15 ml bottle.

(2) The pellet of cells is then resuspended in 350 µl of the following buffer:

| | |
|---|---|
| Tris/HCl pH 8.0 | 20 mM |
| EDTA | 50 mM |
| NaCl | 100 mM. |

(3) Add 50 µl of proteinase K from a stock solution at 2 mg/ml (if unavailable, it is possible to use pronase at 10 mg/ml).

(4) Add 25 µl of SDS at 20% and incubate for 2 hours at 55° C.

(5) Add 2 µl of diethylpyrocarbonate (DEPC) and incubate for 15 min at 70° C.

(6) Cool the tube briefly in ice and add 50 µl of 5 M solution of potassium acetate.

(7) Mix, by shaking the tube correctly, and leave on ice for at least 30 min (it is possible to stop the extraction at that moment and resume on the next day if the tubes are left in ice in a coldroom).

(8) Transfer to a 1.5 ml Eppendorf tube and centrifuge for 15 min in a minicentrifuge (at about 13000 g).

(9) Recover the supernatant, transferring it to a new Eppendorf tube.

(10) Extract the supernatant with one volume of the following mixture:

| | |
|---|---|
| Phenol (saturated with TE: Tris/HCl pH 8.0 10 mM, EDTA 1 mM) | 25 vol |
| Chloroform | 24 vol |
| Isoamyl alcohol | 1 vol |

(11) After extraction, add 1 ml of 100% ethanol at room temperature. A precipitate should be seen to appear in the form of "angel hair" if extraction is successful. From this moment, manipulations must be careful and gentle so that the DNA molecules do not break.

(12) Centrifuge for 5 min in a minicentrifuge (about 13000 g).

(13) Rinse the pellet with 70% ethanol and centrifuge for 3 min in a minicentrifuge.

(14) Repeat operation (13) once or twice for proper elimination of the salts.

(15) Dry the pellet for 5 min at 37° C., then dissolve it in 50 µl of TE containing bovine pancreas RNase at 1 µg/ml.

Molecular hybridizations and Southern Blot analyses: 25 µg of DNA is digested completely with the appropriate restriction endonuclease(s). The restriction products are then separated by electrophoresis in 0.8% agarose gel, TBE×1. Then the gel is incubated successively for 15 min in the depurination solution and for 30 min in the denaturing solution. The denatured DNA is then transferred onto "Porablot NYplus" nylon membrane (Macherey-Nagel GmbH, Düiren, Germany) by capillarity with SSC buffer×20. After transfer, the membrane is incubated at 80° C. in absence of air for 2 hours to fix the DNA fragments to the surface of the nylon membrane. Prehybridization is effected in the hybridization buffer at 42° C. for at least 4 hours. Hybridization is accomplished at 42° C. for a whole night in the presence of the labelled probe prepared previously. The membrane is washed at 60° C. in the washing buffer adjusted to the stringency that is to be applied to the washing. The time and frequency of replacement of the washing baths vary depending on the stringency and the levels of radioactivity present on the membrane. In general, the baths are renewed every 10 min and washing begins with a washing buffer of low stringency and ends with a buffer of higher stringency. A Kodak X-OMAT AR film is finally exposed to the membrane at −80° C. to reveal the hybridization zones.

II) Investigation of Binding of the GBSSI to the Starch Granule.

A) Analysis of the sta2-1 Mutant Allele

Among all the mutant alleles generated at the STA2 locus in *C. reinhardtii*, just one leads to the production of a 58 kDa truncated GBSSI in place of the 76 kDa wild protein. This is the sta2-1 allele of the 18B strain. Delrue et al. (1992), by micro-sequencing of the GBSSI extracted from a polyacrylamide gel, were able to demonstrate that the amino terminal peptide sequences of the proteins of the wild strain (137C) and of the mutant strain (18B) are identical.

Amino terminal sequences:

ρ GBSSI of the 137C strain: ALDIVMVAAEVAPGGK-TGGLGDV (SEQ ID NO:13)

ρ GBSSI of the 18B strain: ALDIVMVAAEVAPGGK-TGGLGDV (SEQ ID NO:13)

The protein produced by the sta2-1 mutant allele is therefore truncated in the carboxy terminal position and the $K_m$ for ADP-glucose is increased by a factor of 6. Absence of this carboxy terminal sequence does not, however, alter the properties of fixation of the protein on the granule, as is shown in FIG. 1.

Detailed Protocol:

Technique of extraction of the proteins from the starch granule and SDS-PAGE: the proteins are extracted from 0.3 to 1 mg of starch with 60 µl of extraction buffer: β-mercaptoethanol 5% (v/v); SDS 2% (w/v) at 100° C. for 5 min. After centrifugation at 13000 g for 10 min, the supernatant is recovered and the operation is repeated once with the pellet. The two supernatants are combined and the sample can be loaded into the gel wells after adding again 10 µl of the following loading buffer: Tris 50 mM, glycine 384 mM, 20% glycerol, SDS 0.1%, bromophenol blue 0.001%. Migration is carried out at room temperature, at 150 V for 1 h 30 (until the bromophenol blue leaves the gel). The proteins are revealed by staining with Coomassie blue or by immunodetection (see below; section relating to Western Blot). During staining with Coomassie blue, the gel is incubated for 30 min in the following solution: 2 g of Coomassie Brilliant Blue R250, 0.5 g of Coomassie Brilliant Blue G250, 425 ml of ethanol, 50 ml of methanol, 100 ml of acetic acid; water sufficient for 1000 ml. The gel is then decolorized using the following solutions:

15 to 30 min in decolorizer I: 450 ml of ethanol, 50 ml of acetic acid; make up to 1000 ml with water.

one night in decolorizer II: 80 ml of acetic acid, 50 ml of methanol, make up to 1000 ml with water; this decolorizer II removes the nonspecific coloration of the gel.

decolorizer III (240 ml of acetic acid, 200 ml of methanol, make up to 1000 ml with water) permits complete decolorizing of the gel if necessary.

B) Determination of the Quantity of Proteins Bound to the Granule

The quantity of proteins bound to the starch granule was determined in different culture conditions and in various gene libraries. For this, the cells were placed in conditions of massive accumulation of starch (nitrogen-deficient medium) or in conditions of mixotrophic growth (presence of nitrogen). The proteins extracted from the granule were then deposited on polyacrylamide gel in denaturing conditions (presence of SDS). After migration, the proteins are revealed by staining with Coomassie blue. The 17 strain, mutant at the STA1 locus, was used during this experiment. This mutation was described in detail by Van den Koornhuyse et al. (1996) and then by Van de Wal et al. (1998). The STA1 locus corresponds to the structural gene of the large regulatory subunit of ADP-glucose pyrophosphorylase. The sta1-1 mutation produced during X-ray mutagenesis leads to insensitivity of the enzyme to 3-phosphoglyceric acid, its allosteric activator. Consequently, the 17 strain accumulates less than 5% of the normal quantity of starch. The estimate of the quantity of GBSSI bound to the granule is approx. 0.1% of the weight of starch in conditions of nitrogen deficiency for the 137C and 18B strains. This value reaches 1% in conditions of mixotrophy. In the case of the 17 strain, regardless of the culture conditions, the GBSSI represents more than 1% of the weight of the starch granule. The techniques employed in this analysis are the same as those described in the preceding paragraph.

C) Analysis of Immune Response in Western Blot

To test the antigenicity of the SA137C and SAIJ2 antisera obtained previously in the rabbit, the proteins extracted from 100 µg of fresh starch obtained from different strains cultivated in variable culture conditions were subjected to analysis by the immunotransfer technique (Western Blotting). The immune response produced with respect to GBSSI during injection of the starch from the wild strain (137C) proves very specific and strong (the proteins having been extracted from just 100 µg of fresh starch) even in the case of the truncated protein in the sta2-1 mutant. The quantity of proteins bound to the starch granule seems larger in the 17 mutant during nitrogen-deficient culture, as shown by the presence of a mass band higher than GBSSI revealed by the SA137C antiserum. This is confirmed by Western Blot analysis effected with the SAIJ2 antiserum, where the strongest immune response is detected with the proteins extracted from the starch of the 17 strain cultivated with nitrogen deficiency.

For control purposes, we carried out the same type of experiment using the PA55 antiserum obtained by Abel et al. (1995). This antiserum produced in the rabbit is directed against a peptide whose consensus sequence corresponds to the strongly conserved carboxy terminal region in all the starch synthases of higher plants, whether they are soluble or bound to the starch granule. This antiserum recognizes the GBSSI of *C. reinhardtii* specifically when the latter is present in the granule. Moreover, the PA55 antiserum also recognizes the truncated protein produced by the 18B mutant (sta2-1). It therefore appears that the highly conserved sequence in carboxy terminal position is still present in the truncated protein.

Detailed Protocols:

Technique of protein extraction from the starch granule and SDS-PAGE: these techniques are the same as those described in the preceding section apart from staining with Coomassie blue, which is omitted in this case.

Technique of transfer and detection with antisera: when migration on SDS-PAGE has ended, the gel is incubated for 30 min in the "Western" buffer×1 containing 20% of methanol. The proteins are then electrotransferred onto a nitrocellulose membrane (Protan BA 85 Schleicher & Schuell, Dassel, Germany) using electrotransfer apparatus (Multiphor II, LKB-Pharmacia, Bromma, Sweden) at 4° C. in the following conditions: 45 min at 250 mA with the buffer used previously. After this stage of transfer of the proteins onto the nitrocellulose membrane, the latter is incubated for 1 hour at room temperature in TBST buffer containing 3% of BSA. The membrane is then rinsed three times in TBST buffer before being incubated overnight at 4° C. in the rabbit primary antiserum diluted in TBS buffer. The membrane is again rinsed three times with TBST buffer and is then incubated for 1 hour at room temperature with the biotinylated secondary antibody diluted at 1/500 in the TBS directed against the rabbit antiserum. After three further rinses in TBST buffer, the membrane is incubated for 30 min at room temperature with the streptavidin-alkaline phosphatase complex at 1/3000 dilution in the TBS buffer. Finally, after 3 rinses in TBST buffer, the membranes are developed by incubation in a diethanolamine buffer containing the substrates of alkaline phosphatase: NBT and BCIP (the incubation time varies depending on the intensity of reaction). The detection kit used is the one offered by Amersham Buehler (Braunschweig, Germany): "Blotting detection kit for rabbit antibodies"

| Compositions of solutions and buffers: | | |
|---|---|---|
| "Western" buffer × 10: | Glycine | 390 mM |
| | Tris | 480 mM |
| | SDS | 0.375% |
| TBS buffer (Tris Buffer Saline) | Tris/HCl pH 7.5 | 20 mM |
| | NaCl | 500 mM |
| TBST buffer (Tris Buffer Saline Tween): TBS + 0.1% (v/v) Tween 20 | | |
| NBT: Nitro-Blue Tetrazolium in solution in dimethylformamide 70% | | |
| BCIP: 5-Bromo-4-Chloro-3-Indolyl Phosphate in solution in dimethylformamide. | | |

III) Targeting of Fusion Proteins in the Starch Granule

The specific carboxy terminal extension of the GBSSI of *C. reinhardtii* is not required for targeting the protein to the starch granule in vivo as we were able to demonstrate in the previous experiments. The extension of about 16 kDa can be replaced by a peptide sequence of interest, thus permitting its targeting to the very heart of the starch granule.

The various types of vectors that can be constructed for applying this method in higher plants consist of:
- a bacterial selector gene and a bacterial replication origin in order to be able to amplify the plasmid in a suitable bacterial strain
- a selector gene that will permit easy selection of transformant plants
- translational fusion between the coding sequence of the GBSSI and a polypeptide sequence of interest. Two main types of translational fusions may be considered: in the first case, it is the 58 kDa truncated sequence from GBSSI that is fused with the sequence of interest; in the second case, the complete sequence of the GBSSI is employed.
- fusion can be put under the control of a strong constitutive plant promoter, or of an inducible plant promoter, immediately followed by a suitable transit peptide promoting translocation of the fusion protein to the chloroplast.

IV) Protocol for Determination of the Activity of Granule-Bound Starch Synthase:

Add 20 µg of starch to 100 µl of the following reaction mixture:

| | |
|---|---|
| Glycylglycine/NaOH pH 9.0 | 50 mM |
| $(NH_4)_2SO_4$ | 100 mM |
| β-mercaptoethanol | 5 mM |
| $MgCl_2$ | 5 mM |
| Bovine serum albumin | 0.5 mg/ml |
| ADP-glucose | 0.2 mM |
| [U $^{14}$C]ADP-glucose (235 mCi/mmol) | 2.66 µg |
| Trisodium citrate | 0 or 0.5 M (specified depending on circumstances) |

The reaction is carried out at 30° C. for 15 min and is then stopped by adding 3 ml of 70% ethanol. The precipitate obtained is filtered under vacuum on a "Whatman Glass Fibre" filter (Whatman, Maidstone, UK), and rinsed with 4×5 ml of 70% ethanol. A Beckman counter is used for radioactivity counting after the filters have been placed in counting phials containing 3.5 ml of scintillation liquid.

V) The methods of Starch Extraction and Purification are as Follows:
- in the case of a single-celled green algae such as *Chlamydomonas reinhardtii* (see the method described above)

in the case of seeds, tubers or any other organ of higher plants:

the organ or the type taken from the plant is properly homogenized (after grinding). The pulverized material thus obtained is rinsed with water through a filter cloth (such as Miracloth Calbiochem, La Jolla, Calif., USA). The filtrate is then left to stand for two hours for the starch granules to settle. The sediment is rinsed firstly with several volumes of water then a second time with several volumes of NaCl solution at 0.1 M. The sediment is filtered once again then rinsed twice with ethanol before being dried.

BIBLIOGRAPHY

Abel G., Springer F., Willmitzer L. and Kossmann J., (1996), *The Plant Journal*, 10 (6): 981–991

An et al. (1986), *Plant Physiol.*, 81, 301–305

Baba T., Nishihara M., Mizuno K., Kawasaki T., Shimada H., Kobayashi E., Ohnishi S., Tanaka K. and Arai Y., (1993), *Plant Physiology*, 103: 565–573

Bevan M. (1984), *Nucleic Acids. Res.*, 12, 8711–8721

Brodelius et al. (1979), *FEBS Letters*, 103, 93–97

Brodelius (1988), In: Moo-Young M. (Ed), *Bioreactor Immobilized Enzymes and Cells: Fundamentals and Applications*, Elsevier, Londres Buléon A., Colonna P., Planchot V., Ball S. (1998), *International Journal of Biological Macromolecules*, 23: 85–112

De La Penna et al. (1987), *Nature*, 325, 274–276

Delrue B., Fontaine T., Routier F., Decq A., Wieruszeski J-M, van den Koornhuyse N., Maddelein M-L., Fournet B. and Ball S. (1992), *Journal of Bacteriology*, 174 (11): 3612–3620

Deno et al (1987), *J Plant. Physiol.*, 131, 315–322

Denyer K., Clarke B., Hylton C., Tatge H. and Smith A., (1996), *Plant, Cell and Environment*, 18: 1019–1026

Denyer K., Hylton C. and Smith A., (1995), *Planta*, 196: 256–265

Dry I., Smith A., Edwards A., Battacharyya M., Dunn P. and Martin C. (1992), *The Plant Journal*, 2 (2): 193–202

Edwards A., Marshall J., Sidebottom C., Visser R., Smith A. and Martin C. (1995), *The Plant Journal*, 8 (2): 283–294

Fontaine T., D'Hulst C., Maddelein M-L, Routier F., Marianne Pepin T., Decq A., Wieruszeski J-M., Delrue B., van den Koornhuyse N., Bossu J-P., Fournet B. and Ball S., (1993), *The Journal of Biological Chemistry*, 268 (22): 16223–16230

Gao M., Wanat J., Stinard P. S., James M. G., Myers A. M. (1998) *Plant Cell*, 10(3): 399–412

Hovenkamp-Hermelink J., Jacobsen E., Ponstein A., Visser R., Vos-Scheperkeuter G., Bijmolt E., de Vries J., Witholt B. and Feenstra W. (1987), *Theoretical and Applied Genetics*, 75: 217–221

Jouanin et al. (1987), *Plant Sci.*, 53, 53–63

MacDonald F. and Preiss J., (1985), *Plant Physiology*, 78: 849–852

Maddelein M-L., Libessart N., Bellanger F., Delrue B., D'Hulst C., van den Koomhuyse N., Fontaine T., Wieruszeski J-M., Decq A. and Ball S., (1994), *The Journal of Biological Chemistry*, 269 (40): 25150–25157

Marshall J., Sidebottom C., Debet M., Martin C., Smith A. and Edwards A., (1996), *The Plant Cell*, 8: 1121–1135

Mu C., Ham C., Ko Y-T., Singletary G., Keeling P. and Wasserman B., (1994), *The Plant Journal*, 6 (2): 151–159

Müller-Röber B., Sonnewald U. and Willmitzer L. (1992), *The EMBO Journal*, 11(4): 1229–1238

Rochaix J., Mayfield S., Goldschlmidt-Clermont M. and Erickson J., (1991), *Plant Molecular Biology: a Practical Approach*, pp 253–275, ed. Shaw C., IRL Press, Oxford Sanford J. C. (1988), *Trends in Biotechnology*, 6, 299–302

Shannon J. and Garwood D. (1984), In *Starch: Chemistry and Technology*, 2nd ed., Whistler R., Bemiller J., Paschall E., eds., Academic Press, San Diego, Calif.: 26–86

Smith A., (1990), *Planta*, 182: 599–604

Tsai C—Y., (1974), *Biochemical Genetics*, 11 (2): 83–95

Van den Koornhuyse N., Libessart N., Delrue B., Zabawinski C., Decq A., Iglesias A., Carton A., Preiss J. and Ball S., (1996), *The Journal of Biological Chemistry*, 271(27): 16281–16287

Van de Wal et al (1998), *The Journal of Biological Chemistry*, 273(35): 22232–22240

Zhang H., Herman P. and Weeks D., (1994), *Plant Molecular Biology*, 24: 663–672

---

What is claimed is:

1. A pharmaceutical composition, comprising starch granules containing at least one fusion polypeptide comprising:
In the N terminal position:
the peptide sequence of SEQ ID No: 3 comprising the granule bound starch synthase GBSSI of *Chlamydomonas reinhardtii* or the sequence SEQ ID No: 5 comprising the GBSSI of *Chlamydomonas reinhardtii* in the form of mature protein of 651 amino acids, said sequences being encoded by nucleotide sequences SEQ ID No: 2, and 4 respectively,
and, in the C-terminal position, a peptide or polypeptide of interest, the C-terminal part of the amino acid sequence of the GBSSI thus being bound to the N-terminal part of the peptide sequence of interest,
the said fusion polypeptide being encoded by a recombinant nucleotide sequence containing in the 5'→3' direction, a nucleotide sequence coding for said *Chlamydomonas reinhardtii* GBSSI,
the said nucleotide sequence coding for this enzyme being positioned upstream of a nucleotide sequence coding for the peptide or polypeptide of interest, the peptide of interest in the said fusion polypeptides possessing a defined therapeutic effect.

2. A pharmaceutical composition according to claim 1, containing
the sequence SEQ ID No: 7 or the sequence SEQ ID No: 9,
said sequence being encoded by nucleotide sequences SEQ ID Nos: 6 and 8, respectively.

3. A pharmaceutical composition according to claim 1 wherein the peptide or polypeptide of interest is selected from:
biologically active peptides, or
enzymes that are able to transform starch, such as enzymes that interact with α-glucans including various hydrolases, phosphorylases, α-1,4-glucanotransferases, branching enzymes, amylases.

4. A pharmaceutical composition according to claim 1 wherein the fusion polypeptide comprises a cleavage site positioned between the starch synthase, and the polypeptide of interest.

5. A pharmaceutical composition according to claim 1, wherein the diameter of the starch granules are between about 0.1 μm and of 10 μm, and the proportion by weight of the fusion polypeptides in these granules are between about 0.1% and 1%.

6. A pharmaceutical composition containing at least one fusion polypeptide comprising:
in the N-terminal position:
the peptide sequence SEQ ID No: 3 or the sequence SEQ ID No: 5 said sequence being encoded by nucleotide sequences SEQ ID Nos: 2 and 4, respectively,
and, in the C-terminal position, a peptide or polypeptide of interest, the C-terminal part of the amino acid sequence of the GBSSI thus being bound to the N-terminal part of the peptide sequence of interest,
the said fusion polypeptide being encoded by a recombinant nucleotide sequence containing in the 5'→3' direction, a nucleotide sequence coding for said *Chlamydomonas reinhardtii* GBSSI,
the said nucleotide sequence coding for this enzyme being positioned upstream of a nucleotide sequence coding for a peptide or polypeptide of interest, the peptide of interest in the said fusion polypeptides possessing a defined therapeutic effect.

7. A pharmaceutical composition according to claim 6 containing
the sequence SEQ ID No: 7
the sequence SEQ ID No: 9
said sequences being encoded by nucleotide sequences SEQ ID Nos: 6 and 8 respectively.

8. A pharmaceutical composition according to claim 6 wherein the peptide or polypeptide of interest is selected from:
biologically active peptides, or
enzymes that are able to transform starch, such as enzymes that interact with α-glucans including various hydrolases, phosphorylases, α-1,4-glucanotransferases, branching enzymes, amylases.

9. A pharmaceutical composition according to claim 6 wherein the fusion polypeptide comprises a cleavage site positioned between the starch synthase, and the polypeptide of interest.

10. A pharmaceutical composition according to claim 3, wherein the biologically active peptides are peptides of therapeutic interest or peptides that can be used in the agricultural and food industry.

11. A pharmaceutical composition according to claim 3, wherein the enzymes that are able to transform starch are heat-resistant hydrolases obtained from extremophiles such as archaebacteria that are active at temperatures above 12° C.

12. A pharmaceutical composition according to claim 8, wherein the biologically active peptides are peptides of therapeutic interest or peptides that can be used in the agricultural and food industry.

13. A pharmaceutical composition according to claim 8, wherein the enzymes that are able to transform starch are heat-resistant hydrolases obtained from extremophiles such as archaebacteria that are active at temperatures above 40° C.

* * * * *

SEQUENCE LISTING

<160> NUMBER OF SEQ ID NOS: 15

<210> SEQ ID NO 1
<211> LENGTH: 3117
<212> TYPE: DNA
<213> ORGANISM: Chlamydomonas reinhardtii

<400> SEQUENCE: 1

```
gccaggcgga gcgtatggct gttgcctcta ccagccgccc cagcagcgcg cgtcctatcg      60
tcatcaatgc cgcgtcgttc ggtgtcaaga agaccgcgaa ccagctgctg cgtgagcttg     120
ctcgtggctc cgcacgcaag tccacctcgc gctcggctgt tactggtgcc actggtgcca     180
cttgcgcgct ggacatcgtg atggttgctg ctgaggtcgc cccttggtcc aagacgggcg     240
gcctgggcga tgtgactggt ggcctgccta ttgagctggt caagcgcggc caccgcgtca     300
tgaccattgc ccctcgctac gaccagtacg ctgacgcctg ggacacctcg gtggtcgtgg     360
acatcatggg cgagaaggtc cgctacttcc actccatcaa gaagggcgtg caccgcgtgt     420
```

-continued

```
ggattgacca cccctggttc ctggccaagg tctggggcaa gaccggctcc aagctgtacg      480
gcccccgctc cggcgctgac tacctggaca accacaagcg cttcgccctg ttctgcaagg      540
ccgctattga ggctgcccgc gtgctgccct cggccccgg cgaggactgc gtcttcgtgg       600
ccaacgactg gcactccgcc ctggtgcccg tcctgctgaa ggacgagtac cagcccaagg      660
gccagttcac caaggccaag tcggtgctgg ctatccacaa catcgccttc cagggccgca      720
tgtgggagga ggctttcaag gacacgaagc tgccccaggc cgcctttgac aagctggcct      780
tctcggacgg ctatgccaag gtttacactg aggccacccc catggaggag gacgagaagc      840
ccccgctgac gggaaagacc tacaagaaga tcaactggct gaagggtggc attatcgccg      900
ccgacaagct ggtgactgtg tcgcccaact acgcgaccga gatcgctgcc gatgccgccg      960
gcggtgtgga gctggacacc gtcatccgcg ccaagggcat tgagggcatt gtgaacggca      1020
tggacattga ggagtggaac cccaagaccg acaagttcct gtctgcgccc tacgaccaga      1080
acagcgtcta cgccggcaag gccgccgcca aggaggccct gcaggccgag ctgggcctgc      1140
ctgtggaccc caccgccccc ctgttcgcct tcatcggccg cctggaggag cagaaggtgt      1200
gggacatcat cctggccgcc ctgcccaaga tcctggccac cccaaggtg cagatcgcca      1260
tcctgggtac cggcaaggcc gcctacgaga agctggtgaa cgccatcggc accaagtaca      1320
agggccgcgc caagggcgtg gtcaagttct cggcgcccct ggcgcacatg ctcaccgccg      1380
gcgccgactt catgctggtg ccctcgcgct tcgagccctg cggcctgatc cagctgcacg      1440
ccatgcacta cggtaccgtg cccgtggtag cctccaccgg cggcctggtc gacaccgtca      1500
aggagggcgt caccggcttc cacatgggcg ccctgaaccc cgacaagctg gacgaggctg      1560
acgccgacgc cctggccgcc accgtgcgcc gtgccacgca ggtgtttgcg ggcggccgct      1620
accccgagat ggtggccaac tgcatcagcc aggacctgtc ctggtccaag cccgcccaga      1680
agtgggaggg cctgctggag gaggtggtgt acggcaaggg cggcgtggcc accgccaaga      1740
aggaggagat caaggtgccc gttgccgaga agatccccgg cgacctgccc gccgtgtcct      1800
acgcccccaa cacctgaag cccgtgtccg cctccgtgga gggcaacggc gccgccgcgc      1860
ccaaggtcgg caccaccgcc cccgccatgg gcgcgtggcg cgcgaccacc ccctcgggcc      1920
cctcgcccgc cgccgccacc cccaaggtga ccacctacaa gcccgccctg cccgccaccg      1980
ccaagcccaa gaccgctggc ctcaagctgg ccggtgaggc ctccaccacc tcgacctcgg      2040
agaacggcgc tgcctccaac ggcaacggca acggtgcctc ggcctccaag acctcggctg      2100
ccaagcccct ggtctccgcc gccacccgca gtccgcccta aagcggcagt agccgcagag      2160
gcggcgacag catgagcggc tcgaccaaag ctgtggcagg aacggctgta gcagcggcag      2220
gcggccgcca ccggcgagga gcaggcttgc ggcagcgagg gcgatgagct tagcggccgt      2280
gagcatggca ggcggaaacg tgtgtactga aatgtggtgc atgagagtgt cgtgctgtaa      2340
tgaagtcggt tttgcgagac cggagaaacg ccggtttggt tttgtagtgc agggcctgtg      2400
gtttcggttt tgcccaagtc caaaagaaga gtaacgaaac tgtagcagta gcagagcact      2460
tgcgcggcgc ggcgaccacg ccggcccgtg cgcagcctgt cctgccctca gccttgtgat      2520
tcggcggcaa gagggcgggt ctgtacactc catccattcc aggattttg caggctgcct       2580
gagagtttgc cattttgtgg gacgtgagcg gcggacggc cgcgcgggc tctcctaccg        2640
cctccggcaa cggagaagtg ggaggcgctg tagcccggtg acccccaat gtagaggatg       2700
ggatacataa gagcgtgtgg aatggtggta aagaggagg ggcctgggtc gccctcgat        2760
```

```
ggttttgttg aggtgcagac ggcaccgtcg gcgtcaaagg ccctcgcaag gcccgggtgc    2820
cttgggctca ttttggtgc ccgtcgatga tgagagattg gccagcggtt ttttgaggct    2880
ggctcgaagc gagggtttgt ggaagtggag cgaggagggt tggagaaaga ggcggacatg    2940
cttgactgga ggtacacaaa gtggagcgtg cgacggcacg gaggcattgg cggactattg    3000
acccagtagt gtggaaagta gttggacctg aattctttga gagtaccgcg cattaatccg    3060
tgagagagta acaagatgg cacctgaaaa aaaaaaaaaa aaaaaaaaaa aaaaaa        3117
```

<210> SEQ ID NO 2
<211> LENGTH: 2124
<212> TYPE: DNA
<213> ORGANISM: Chlamydomonas reinhardtii
<220> FEATURE:
<223> OTHER INFORMATION: Fragment of the complete sequence of cDNA
      coding for the GBSSI of Chlamydomonas reinhardtii
<220> FEATURE:
<221> NAME/KEY: CDS
<222> LOCATION: (1)..(2124)

<400> SEQUENCE: 2

```
atg gct gtt gcc tct acc agc cgc ccc agc agc gcg cgt cct atc gtc      48
Met Ala Val Ala Ser Thr Ser Arg Pro Ser Ser Ala Arg Pro Ile Val
 1               5                  10                  15 atc aat gcc gcg tcg ttc ggt gtc aag aag acc gcg aac cag ctg ctg      96
Ile Asn Ala Ala Ser Phe Gly Val Lys Lys Thr Ala Asn Gln Leu Leu
             20                  25                  30 cgt gag ctt gct cgt ggc tcc gca cgc aag tcc acc tcg cgc tcg gct     144
Arg Glu Leu Ala Arg Gly Ser Ala Arg Lys Ser Thr Ser Arg Ser Ala
         35                  40                  45 gtt act ggt gcc act ggt gcc act tgc gcg ctg gac atc gtg atg gtt     192
Val Thr Gly Ala Thr Gly Ala Thr Cys Ala Leu Asp Ile Val Met Val
     50                  55                  60 gct gct gag gtc gcc cct tgg tcc aag acg ggc ggc ctg ggc gat gtg     240
Ala Ala Glu Val Ala Pro Trp Ser Lys Thr Gly Gly Leu Gly Asp Val
 65                  70                  75                  80 act ggt ggc ctg cct att gag ctg gtc aag cgc ggc cac cgc gtc atg     288
Thr Gly Gly Leu Pro Ile Glu Leu Val Lys Arg Gly His Arg Val Met
                 85                  90                  95 acc att gcc cct cgc tac gac cag tac gct gac gcc tgg gac acc tcg     336
Thr Ile Ala Pro Arg Tyr Asp Gln Tyr Ala Asp Ala Trp Asp Thr Ser
            100                 105                 110 gtg gtc gtg gac atc atg ggc gag aag gtc cgc tac ttc cac tcc atc     384
Val Val Val Asp Ile Met Gly Glu Lys Val Arg Tyr Phe His Ser Ile
        115                 120                 125 aag aag ggc gtg cac cgc gtg tgg att gac cac ccc tgg ttc ctg gcc     432
Lys Lys Gly Val His Arg Val Trp Ile Asp His Pro Trp Phe Leu Ala
    130                 135                 140 aag gtc tgg ggc aag acc ggc tcc aag ctg tac ggc ccc cgc tcc ggc     480
Lys Val Trp Gly Lys Thr Gly Ser Lys Leu Tyr Gly Pro Arg Ser Gly
145                 150                 155                 160 gct gac tac ctg gac aac cac aag cgc ttc gcc ctg ttc tgc aag gcc     528
Ala Asp Tyr Leu Asp Asn His Lys Arg Phe Ala Leu Phe Cys Lys Ala
                165                 170                 175 gct att gag gct gcc cgc gtg ctg ccc ttc ggc ccc ggc gag gac tgc     576
Ala Ile Glu Ala Ala Arg Val Leu Pro Phe Gly Pro Gly Glu Asp Cys
            180                 185                 190 gtc ttc gtg gcc aac gac tgg cac tcc gcc ctg gtg ccc gtc ctg ctg     624
Val Phe Val Ala Asn Asp Trp His Ser Ala Leu Val Pro Val Leu Leu
        195                 200                 205 aag gac gag tac cag ccc aag ggc cag ttc acc aag gcc aag tcg gtg     672
```

```
                Lys Asp Glu Tyr Gln Pro Lys Gly Gln Phe Thr Lys Ala Lys Ser Val
                    210                 215                 220 ctg gct atc cac aac atc gcc ttc cag ggc cgc atg tgg gag gag gct          720
Leu Ala Ile His Asn Ile Ala Phe Gln Gly Arg Met Trp Glu Glu Ala
225                 230                 235                 240 ttc aag gac acg aag ctg ccc cag gcc gcc ttt gac aag ctg gcc ttc          768
Phe Lys Asp Thr Lys Leu Pro Gln Ala Ala Phe Asp Lys Leu Ala Phe
                245                 250                 255 tcg gac ggc tat gcc aag gtt tac act gag gcc acc ccc atg gag gag          816
Ser Asp Gly Tyr Ala Lys Val Tyr Thr Glu Ala Thr Pro Met Glu Glu
            260                 265                 270 gac gag aag ccc ccg ctg acg gga aag acc tac aag aag atc aac tgg          864
Asp Glu Lys Pro Pro Leu Thr Gly Lys Thr Tyr Lys Lys Ile Asn Trp
        275                 280                 285 ctg aag ggt ggc att atc gcc gcc gac aag ctg gtg act gtg tcg ccc          912
Leu Lys Gly Gly Ile Ile Ala Ala Asp Lys Leu Val Thr Val Ser Pro
    290                 295                 300 aac tac gcg acc gag atc gct gcc gat gcc gcc ggc ggt gtg gag ctg          960
Asn Tyr Ala Thr Glu Ile Ala Ala Asp Ala Ala Gly Gly Val Glu Leu
305                 310                 315                 320 gac acc gtc atc cgc gcc aag ggc att gag ggc att gtg aac ggc atg         1008
Asp Thr Val Ile Arg Ala Lys Gly Ile Glu Gly Ile Val Asn Gly Met
                325                 330                 335 gac att gag gag tgg aac ccc aag acc gac aag ttc ctg tct gcg ccc         1056
Asp Ile Glu Glu Trp Asn Pro Lys Thr Asp Lys Phe Leu Ser Ala Pro
            340                 345                 350 tac gac cag aac agc gtc tac gcc ggc aag gcc gcc gcc aag gag gcc         1104
Tyr Asp Gln Asn Ser Val Tyr Ala Gly Lys Ala Ala Ala Lys Glu Ala
        355                 360                 365 ctg cag gcc gag ctg ggc ctg cct gtg gac ccc acc gcc ccc ctg ttc         1152
Leu Gln Ala Glu Leu Gly Leu Pro Val Asp Pro Thr Ala Pro Leu Phe
    370                 375                 380 gcc ttc atc ggc cgc ctg gag gag cag aag ggt gtg gac atc atc ctg         1200
Ala Phe Ile Gly Arg Leu Glu Glu Gln Lys Gly Val Asp Ile Ile Leu
385                 390                 395                 400 gcc gcc ctg ccc aag atc ctg gcc acc ccc aag gtg cag atc gcc atc         1248
Ala Ala Leu Pro Lys Ile Leu Ala Thr Pro Lys Val Gln Ile Ala Ile
                405                 410                 415 ctg ggt acc ggc aag gcc gcc tac gag aag ctg gtg aac gcc atc ggc         1296
Leu Gly Thr Gly Lys Ala Ala Tyr Glu Lys Leu Val Asn Ala Ile Gly
            420                 425                 430 acc aag tac aag ggc cgc gcc aag ggc gtg gtc aag ttc tcg gcg ccc         1344
Thr Lys Tyr Lys Gly Arg Ala Lys Gly Val Val Lys Phe Ser Ala Pro
        435                 440                 445 ctg gcg cac atg ctc acc gcc ggc gcc gac ttc atg ctg gtg ccc tcg         1392
Leu Ala His Met Leu Thr Ala Gly Ala Asp Phe Met Leu Val Pro Ser
    450                 455                 460 cgc ttc gag ccc tgc ggc ctg atc cag ctg cac gcc atg cac tac ggt         1440
Arg Phe Glu Pro Cys Gly Leu Ile Gln Leu His Ala Met His Tyr Gly
465                 470                 475                 480 acc gtg ccc gtg gta gcc tcc acc ggc ggc ctg gtc gac acc gtc aag         1488
Thr Val Pro Val Val Ala Ser Thr Gly Gly Leu Val Asp Thr Val Lys
                485                 490                 495 gag ggc gtc acc ggc ttc cac atg ggc gcc ctg aac ccc gac aag ctg         1536
Glu Gly Val Thr Gly Phe His Met Gly Ala Leu Asn Pro Asp Lys Leu
            500                 505                 510 gac gag gct gac gcc gac gcc ctg gcc gcc acc gtg cgc cgt gcc agc         1584
Asp Glu Ala Asp Ala Asp Ala Leu Ala Ala Thr Val Arg Arg Ala Ser
        515                 520                 525
```

```
gag gtg ttt gcg ggc ggc cgc tac ccc gag atg gtg gcc aac tgc atc    1632
Glu Val Phe Ala Gly Gly Arg Tyr Pro Glu Met Val Ala Asn Cys Ile
    530                 535                 540 agc cag gac ctg tcc tgg tcc aag ccc gcc cag aag tgg gag ggc ctg    1680
Ser Gln Asp Leu Ser Trp Ser Lys Pro Ala Gln Lys Trp Glu Gly Leu
545                 550                 555                 560 ctg gag gag gtg gtg tac ggc aag ggc ggc gtg gcc acc gcc aag aag    1728
Leu Glu Glu Val Val Tyr Gly Lys Gly Gly Val Ala Thr Ala Lys Lys
                565                 570                 575 gag gag atc aag gtg ccc gtt gcc gag aag atc ccc ggc gac ctg ccc    1776
Glu Glu Ile Lys Val Pro Val Ala Glu Lys Ile Pro Gly Asp Leu Pro
            580                 585                 590 gcc gtg tcc tac gcc ccc aac acc ctg aag ccc gtg tcc gcc tcc gtg    1824
Ala Val Ser Tyr Ala Pro Asn Thr Leu Lys Pro Val Ser Ala Ser Val
        595                 600                 605 gag ggc aac ggc gcc gcc gcg ccc aag gtc ggc acc acc gcc ccc gcc    1872
Glu Gly Asn Gly Ala Ala Ala Pro Lys Val Gly Thr Thr Ala Pro Ala
    610                 615                 620 atg ggc gcg tgg cgc gcg acc acc ccc tcg ggc ccc tcg ccc gcc gcc    1920
Met Gly Ala Trp Arg Ala Thr Thr Pro Ser Gly Pro Ser Pro Ala Ala
625                 630                 635                 640 gcc acc ccc aag gtg acc acc tac aag ccc gcc ctg ccc gcc acc gcc    1968
Ala Thr Pro Lys Val Thr Thr Tyr Lys Pro Ala Leu Pro Ala Thr Ala
                645                 650                 655 aag ccc aag acc gct ggc ctc aag ctg gcc ggt gag gcc tcc acc acc    2016
Lys Pro Lys Thr Ala Gly Leu Lys Leu Ala Gly Glu Ala Ser Thr Thr
            660                 665                 670 tcg acc tcg gag aac ggc gct gcc tcc aac ggc aac ggc aac ggt gcc    2064
Ser Thr Ser Glu Asn Gly Ala Ala Ser Asn Gly Asn Gly Asn Gly Ala
        675                 680                 685 tcg gcc tcc aag acc tcg gct gcc aag ccc ctg gtc tcc gcc gcc acc    2112
Ser Ala Ser Lys Thr Ser Ala Ala Lys Pro Leu Val Ser Ala Ala Thr
    690                 695                 700 cgc aag tcc gcc                                                    2124
Arg Lys Ser Ala
705
```

<210> SEQ ID NO 3
<211> LENGTH: 708
<212> TYPE: PRT
<213> ORGANISM: Chlamydomonas reinhardtii

<400> SEQUENCE: 3

```
Met Ala Val Ala Ser Thr Ser Arg Pro Ser Ser Ala Arg Pro Ile Val
 1               5                  10                  15

Ile Asn Ala Ala Ser Phe Gly Val Lys Lys Thr Ala Asn Gln Leu Leu
            20                  25                  30

Arg Glu Leu Ala Arg Gly Ser Ala Arg Lys Ser Thr Ser Arg Ser Ala
        35                  40                  45

Val Thr Gly Ala Thr Gly Ala Thr Cys Ala Leu Asp Ile Val Met Val
    50                  55                  60

Ala Ala Glu Val Ala Pro Trp Ser Lys Thr Gly Gly Leu Gly Asp Val
65                  70                  75                  80

Thr Gly Gly Leu Pro Ile Glu Leu Val Lys Arg Gly His Arg Val Met
                85                  90                  95

Thr Ile Ala Pro Arg Tyr Asp Gln Tyr Ala Asp Ala Trp Asp Thr Ser
            100                 105                 110

Val Val Val Asp Ile Met Gly Glu Lys Val Arg Tyr Phe His Ser Ile
        115                 120                 125
```

-continued

```
Lys Lys Gly Val His Arg Val Trp Ile Asp His Pro Trp Phe Leu Ala
    130                 135                 140
Lys Val Trp Gly Lys Thr Gly Ser Lys Leu Tyr Gly Pro Arg Ser Gly
145                 150                 155                 160
Ala Asp Tyr Leu Asp Asn His Lys Arg Phe Ala Leu Phe Cys Lys Ala
                165                 170                 175
Ala Ile Glu Ala Ala Arg Val Leu Pro Phe Gly Pro Gly Glu Asp Cys
            180                 185                 190
Val Phe Val Ala Asn Asp Trp His Ser Ala Leu Val Pro Val Leu Leu
        195                 200                 205
Lys Asp Glu Tyr Gln Pro Lys Gly Gln Phe Thr Lys Ala Lys Ser Val
    210                 215                 220
Leu Ala Ile His Asn Ile Ala Phe Gln Gly Arg Met Trp Glu Glu Ala
225                 230                 235                 240
Phe Lys Asp Thr Lys Leu Pro Gln Ala Ala Phe Asp Lys Leu Ala Phe
                245                 250                 255
Ser Asp Gly Tyr Ala Lys Val Tyr Thr Glu Ala Thr Pro Met Glu Glu
            260                 265                 270
Asp Glu Lys Pro Pro Leu Thr Gly Lys Thr Tyr Lys Lys Ile Asn Trp
        275                 280                 285

Leu Lys Gly Gly Ile Ile Ala Ala Asp Lys Leu Val Thr Val Ser Pro
    290                 295                 300

Asn Tyr Ala Thr Glu Ile Ala Ala Asp Ala Ala Gly Gly Val Glu Leu
305                 310                 315                 320
Asp Thr Val Ile Arg Ala Lys Gly Ile Glu Gly Ile Val Asn Gly Met
                325                 330                 335
Asp Ile Glu Glu Trp Asn Pro Lys Thr Asp Lys Phe Leu Ser Ala Pro
            340                 345                 350

Tyr Asp Gln Asn Ser Val Tyr Ala Gly Lys Ala Ala Ala Lys Glu Ala
        355                 360                 365
Leu Gln Ala Glu Leu Gly Leu Pro Val Asp Pro Thr Ala Pro Leu Phe
    370                 375                 380
Ala Phe Ile Gly Arg Leu Glu Glu Gln Lys Gly Val Asp Ile Ile Leu
385                 390                 395                 400
Ala Ala Leu Pro Lys Ile Leu Ala Thr Pro Lys Val Gln Ile Ala Ile
                405                 410                 415
Leu Gly Thr Gly Lys Ala Ala Tyr Glu Lys Leu Val Asn Ala Ile Gly
            420                 425                 430
Thr Lys Tyr Lys Gly Arg Ala Lys Gly Val Val Lys Phe Ser Ala Pro
        435                 440                 445
Leu Ala His Met Leu Thr Ala Gly Ala Asp Phe Met Leu Val Pro Ser
    450                 455                 460
Arg Phe Glu Pro Cys Gly Leu Ile Gln Leu His Ala Met His Tyr Gly
465                 470                 475                 480
Thr Val Pro Val Val Ala Ser Thr Gly Gly Leu Val Asp Thr Val Lys
                485                 490                 495
Glu Gly Val Thr Gly Phe His Met Gly Ala Leu Asn Pro Asp Lys Leu
            500                 505                 510
Asp Glu Ala Asp Ala Asp Ala Leu Ala Ala Thr Val Arg Arg Ala Ser
        515                 520                 525
Glu Val Phe Ala Gly Gly Arg Tyr Pro Glu Met Val Ala Asn Cys Ile
    530                 535                 540
```

-continued

```
Ser Gln Asp Leu Ser Trp Ser Lys Pro Ala Gln Lys Trp Glu Gly Leu
545                 550                 555                 560

Leu Glu Glu Val Val Tyr Gly Lys Gly Gly Val Ala Thr Ala Lys Lys
                565                 570                 575

Glu Glu Ile Lys Val Pro Val Ala Glu Lys Ile Pro Gly Asp Leu Pro
            580                 585                 590

Ala Val Ser Tyr Ala Pro Asn Thr Leu Lys Pro Val Ser Ala Ser Val
                595                 600                 605

Glu Gly Asn Gly Ala Ala Pro Lys Val Gly Thr Thr Ala Pro Ala
            610                 615                 620

Met Gly Ala Trp Arg Ala Thr Thr Pro Ser Gly Pro Ser Pro Ala Ala
625                 630                 635                 640

Ala Thr Pro Lys Val Thr Thr Tyr Lys Pro Ala Leu Pro Ala Thr Ala
                645                 650                 655

Lys Pro Lys Thr Ala Gly Leu Lys Leu Ala Gly Glu Ala Ser Thr Thr
                660                 665                 670

Ser Thr Ser Glu Asn Gly Ala Ala Ser Asn Gly Asn Gly Asn Gly Ala
            675                 680                 685

Ser Ala Ser Lys Thr Ser Ala Ala Lys Pro Leu Val Ser Ala Ala Thr
            690                 695                 700

Arg Lys Ser Ala
705
```

```
<210> SEQ ID NO 4
<211> LENGTH: 1953
<212> TYPE: DNA
<213> ORGANISM: Chlamydomonas reinhardtii
<220> FEATURE:
<223> OTHER INFORMATION: Fragment of the complete sequence of cDNA
      coding for the GBSSI of Chlamydomonas reinhardtii and coding for
      the mature BGSSI protein
<220> FEATURE:
<221> NAME/KEY: CDS
<222> LOCATION: (1)..(1953)

<400> SEQUENCE: 4
```

```
gcg ctg gac atc gtg atg gtt gct gct gag gtc gcc cct tgg tcc aag      48
Ala Leu Asp Ile Val Met Val Ala Ala Glu Val Ala Pro Trp Ser Lys
  1               5                  10                  15 acg ggc ggc ctg ggc gat gtg act ggt ggc ctg cct att gag ctg gtc      96
Thr Gly Gly Leu Gly Asp Val Thr Gly Gly Leu Pro Ile Glu Leu Val
             20                  25                  30 aag cgc ggc cac cgc gtc atg acc att gcc cct cgc tac gac cag tac     144
Lys Arg Gly His Arg Val Met Thr Ile Ala Pro Arg Tyr Asp Gln Tyr
         35                  40                  45 gct gac gcc tgg gac acc tcg gtg gtc gtg gac atc atg ggc gag aag     192
Ala Asp Ala Trp Asp Thr Ser Val Val Val Asp Ile Met Gly Glu Lys
     50                  55                  60 gtc cgc tac ttc cac tcc atc aag aag ggc gtg cac cgc gtg tgg att     240
Val Arg Tyr Phe His Ser Ile Lys Lys Gly Val His Arg Val Trp Ile
 65                  70                  75                  80 gac cac ccc tgg ttc ctg gcc aag gtc tgg ggc aag acc ggc tcc aag     288
Asp His Pro Trp Phe Leu Ala Lys Val Trp Gly Lys Thr Gly Ser Lys
                 85                  90                  95 ctg tac ggc ccc cgc tcc ggc gct gac tac ctg gac aac cac aag cgc     336
Leu Tyr Gly Pro Arg Ser Gly Ala Asp Tyr Leu Asp Asn His Lys Arg
            100                 105                 110 ttc gcc ctg ttc tgc aag gcc gct att gag gct gcc cgc gtg ctg ccc     384
Phe Ala Leu Phe Cys Lys Ala Ala Ile Glu Ala Ala Arg Val Leu Pro
        115                 120                 125
```

-continued

| | |
|---|---|
| ttc ggc ccc ggc gag gac tgc gtc ttc gtg gcc aac gac tgg cac tcc<br>Phe Gly Pro Gly Glu Asp Cys Val Phe Val Ala Asn Asp Trp His Ser<br>130                                 135                             140 | 432 |
| gcc ctg gtg ccc gtc ctg ctg aag gac gag tac cag ccc aag ggc cag<br>Ala Leu Val Pro Val Leu Leu Lys Asp Glu Tyr Gln Pro Lys Gly Gln<br>145                               150                           155                     160 | 480 |
| ttc acc aag gcc aag tcg gtg ctg gct atc cac aac atc gcc ttc cag<br>Phe Thr Lys Ala Lys Ser Val Leu Ala Ile His Asn Ile Ala Phe Gln<br>               165                           170                         175 | 528 |
| ggc cgc atg tgg gag gag gct ttc aag gac acg aag ctg ccc cag gcc<br>Gly Arg Met Trp Glu Glu Ala Phe Lys Asp Thr Lys Leu Pro Gln Ala<br>             180                         185                          190 | 576 |
| gcc ttt gac aag ctg gcc ttc tcg gac ggc tat gcc aag gtt tac act<br>Ala Phe Asp Lys Leu Ala Phe Ser Asp Gly Tyr Ala Lys Val Tyr Thr<br>     195                          200                         205 | 624 |
| gag gcc acc ccc atg gag gag gac gag aag ccc ccg ctg acg gga aag<br>Glu Ala Thr Pro Met Glu Glu Asp Glu Lys Pro Pro Leu Thr Gly Lys<br>210                               215                           220 | 672 |
| acc tac aag aag atc aac tgg ctg aag ggt ggc att atc gcc gcc gac<br>Thr Tyr Lys Lys Ile Asn Trp Leu Lys Gly Gly Ile Ile Ala Ala Asp<br>225                               230                         235                     240 | 720 |
| aag ctg gtg act gtg tcg ccc aac tac gcg acc gag atc gct gcc gat<br>Lys Leu Val Thr Val Ser Pro Asn Tyr Ala Thr Glu Ile Ala Ala Asp<br>                       245                         250                         255 | 768 |
| gcc gcc ggc ggt gtg gag ctg gac acc gtc atc cgc gcc aag ggc att<br>Ala Ala Gly Gly Val Glu Leu Asp Thr Val Ile Arg Ala Lys Gly Ile<br>             260                         265                          270 | 816 |
| gag ggc att gtg aac ggc atg gac att gag gag tgg aac ccc aag acc<br>Glu Gly Ile Val Asn Gly Met Asp Ile Glu Glu Trp Asn Pro Lys Thr<br>     275                          280                         285 | 864 |
| gac aag ttc ctg tct gcg ccc tac gac cag aac agc gtc tac gcc ggc<br>Asp Lys Phe Leu Ser Ala Pro Tyr Asp Gln Asn Ser Val Tyr Ala Gly<br>290                               295                         300 | 912 |
| aag gcc gcc gcc aag gag gcc ctg cag gcc gag ctg ggc ctg cct gtg<br>Lys Ala Ala Ala Lys Glu Ala Leu Gln Ala Glu Leu Gly Leu Pro Val<br>305                               310                         315                     320 | 960 |
| gac ccc acc gcc ccc ctg ttc gcc ttc atc ggc cgc ctg gag gag cag<br>Asp Pro Thr Ala Pro Leu Phe Ala Phe Ile Gly Arg Leu Glu Glu Gln<br>                       325                         330                         335 | 1008 |
| aag ggt gtg gac atc atc ctg gcc gcc ctg ccc aag atc ctg gcc acc<br>Lys Gly Val Asp Ile Ile Leu Ala Ala Leu Pro Lys Ile Leu Ala Thr<br>                           340                         345                         350 | 1056 |
| ccc aag gtg cag atc gcc atc ctg ggt acc ggc aag gcc gcc tac gag<br>Pro Lys Val Gln Ile Ala Ile Leu Gly Thr Gly Lys Ala Ala Tyr Glu<br>                 355                           360                         365 | 1104 |
| aag ctg gtg aac gcc atc ggc acc aag tac aag ggc cgc gcc aag ggc<br>Lys Leu Val Asn Ala Ile Gly Thr Lys Tyr Lys Gly Arg Ala Lys Gly<br>370                               375                         380 | 1152 |
| gtg gtc aag ttc tcg gcg ccc ctg gcg cac atg ctc acc gcc ggc gcc<br>Val Val Lys Phe Ser Ala Pro Leu Ala His Met Leu Thr Ala Gly Ala<br>385                               390                         395                     400 | 1200 |
| gac ttc atg ctg gtg ccc tcg cgc ttc gag ccc tgc ggc ctg atc cag<br>Asp Phe Met Leu Val Pro Ser Arg Phe Glu Pro Cys Gly Leu Ile Gln<br>                       405                         410                         415 | 1248 |
| ctg cac gcc atg cac tac ggt acc gtg ccc gtg gta gcc tcc acc ggc<br>Leu His Ala Met His Tyr Gly Thr Val Pro Val Val Ala Ser Thr Gly<br>             420                         425                          430 | 1296 |
| ggc ctg gtc gac acc gtc aag gag ggc gtc acc ggc ttc cac atg ggc<br>Gly Leu Val Asp Thr Val Lys Glu Gly Val Thr Gly Phe His Met Gly | 1344 |

```
                    435                 440                 445
gcc ctg aac ccc gac aag ctg gac gag gct gac gcc gac gcc ctg gcc    1392
Ala Leu Asn Pro Asp Lys Leu Asp Glu Ala Asp Ala Asp Ala Leu Ala
    450                 455                 460 gcc acc gtg cgc cgt gcc agc gag gtg ttt gcg ggc ggc cgc tac ccc    1440
Ala Thr Val Arg Arg Ala Ser Glu Val Phe Ala Gly Gly Arg Tyr Pro
465                 470                 475                 480 gag atg gtg gcc aac tgc atc agc cag gac ctg tcc tgg tcc aag ccc    1488
Glu Met Val Ala Asn Cys Ile Ser Gln Asp Leu Ser Trp Ser Lys Pro
                485                 490                 495 gcc cag aag tgg gag ggc ctg ctg gag gag gtg gtg tac ggc aag ggc    1536
Ala Gln Lys Trp Glu Gly Leu Leu Glu Glu Val Val Tyr Gly Lys Gly
            500                 505                 510 ggc gtg gcc acc gcc aag aag gag gag atc aag gtg ccc gtt gcc gag    1584
Gly Val Ala Thr Ala Lys Lys Glu Glu Ile Lys Val Pro Val Ala Glu
        515                 520                 525 aag atc ccc ggc gac ctg ccc gcc gtg tcc tac gcc ccc aac acc ctg    1632
Lys Ile Pro Gly Asp Leu Pro Ala Val Ser Tyr Ala Pro Asn Thr Leu
    530                 535                 540 aag ccc gtg tcc gcc tcc gtg gag ggc aac ggc gcc gcc gcg ccc aag    1680
Lys Pro Val Ser Ala Ser Val Glu Gly Asn Gly Ala Ala Ala Pro Lys
545                 550                 555                 560 gtc ggc acc acc gcc ccc gcc atg ggc gcg tgg cgc gcg acc acc ccc    1728
Val Gly Thr Thr Ala Pro Ala Met Gly Ala Trp Arg Ala Thr Thr Pro
                565                 570                 575 tcg ggc ccc tcg ccc gcc gcc gcc acc ccc aag gtg acc acc tac aag    1776
Ser Gly Pro Ser Pro Ala Ala Ala Thr Pro Lys Val Thr Thr Tyr Lys
            580                 585                 590 ccc gcc ctg ccc gcc acc gcc aag ccc aag acc gct ggc ctc aag ctg    1824
Pro Ala Leu Pro Ala Thr Ala Lys Pro Lys Thr Ala Gly Leu Lys Leu
        595                 600                 605 gcc ggt gag gcc tcc acc acc tcg acc tcg gag aac ggc gct gcc tcc    1872
Ala Gly Glu Ala Ser Thr Thr Ser Thr Ser Glu Asn Gly Ala Ala Ser
    610                 615                 620 aac ggc aac ggc aac ggt gcc tcg gcc tcc aag acc tcg gct gcc aag    1920
Asn Gly Asn Gly Asn Gly Ala Ser Ala Ser Lys Thr Ser Ala Ala Lys
625                 630                 635                 640 ccc ctg gtc tcc gcc gcc acc cgc aag tcc gcc                        1953
Pro Leu Val Ser Ala Ala Thr Arg Lys Ser Ala
                645                 650

<210> SEQ ID NO 5
<211> LENGTH: 651
<212> TYPE: PRT
<213> ORGANISM: Chlamydomonas reinhardtii

<400> SEQUENCE: 5

Ala Leu Asp Ile Val Met Val Ala Ala Glu Val Ala Pro Trp Ser Lys
1               5                   10                  15

Thr Gly Gly Leu Gly Asp Val Thr Gly Gly Leu Pro Ile Glu Leu Val
            20                  25                  30

Lys Arg Gly His Arg Val Met Thr Ile Ala Pro Arg Tyr Asp Gln Tyr
        35                  40                  45

Ala Asp Ala Trp Asp Thr Ser Val Val Asp Ile Met Gly Glu Lys
    50                  55                  60

Val Arg Tyr Phe His Ser Ile Lys Lys Gly Val His Arg Val Trp Ile
65                  70                  75                  80

Asp His Pro Trp Phe Leu Ala Lys Val Trp Gly Lys Thr Gly Ser Lys
                85                  90                  95
```

-continued

```
Leu Tyr Gly Pro Arg Ser Gly Ala Asp Tyr Leu Asp Asn His Lys Arg
            100                 105                 110

Phe Ala Leu Phe Cys Lys Ala Ala Ile Glu Ala Ala Arg Val Leu Pro
        115                 120                 125

Phe Gly Pro Gly Glu Asp Cys Val Phe Val Ala Asn Asp Trp His Ser
    130                 135                 140

Ala Leu Val Pro Val Leu Leu Lys Asp Glu Tyr Gln Pro Lys Gly Gln
145                 150                 155                 160

Phe Thr Lys Ala Lys Ser Val Leu Ala Ile His Asn Ile Ala Phe Gln
                165                 170                 175

Gly Arg Met Trp Glu Glu Ala Phe Lys Asp Thr Lys Leu Pro Gln Ala
            180                 185                 190

Ala Phe Asp Lys Leu Ala Phe Ser Asp Gly Tyr Ala Lys Val Tyr Thr
        195                 200                 205

Glu Ala Thr Pro Met Glu Glu Asp Glu Lys Pro Pro Leu Thr Gly Lys
    210                 215                 220

Thr Tyr Lys Lys Ile Asn Trp Leu Lys Gly Ile Ile Ala Ala Asp
225                 230                 235                 240

Lys Leu Val Thr Val Ser Pro Asn Tyr Ala Thr Glu Ile Ala Ala Asp
                245                 250                 255

Ala Ala Gly Gly Val Glu Leu Asp Thr Val Ile Arg Ala Lys Gly Ile
            260                 265                 270

Glu Gly Ile Val Asn Gly Met Asp Ile Glu Glu Trp Asn Pro Lys Thr
        275                 280                 285

Asp Lys Phe Leu Ser Ala Pro Tyr Asp Gln Asn Ser Val Tyr Ala Gly
    290                 295                 300

Lys Ala Ala Lys Glu Ala Leu Gln Ala Glu Leu Gly Leu Pro Val
305                 310                 315                 320

Asp Pro Thr Ala Pro Leu Phe Ala Phe Ile Gly Arg Leu Glu Glu Gln
                325                 330                 335

Lys Gly Val Asp Ile Ile Leu Ala Ala Leu Pro Lys Ile Leu Ala Thr
            340                 345                 350

Pro Lys Val Gln Ile Ala Ile Leu Gly Thr Gly Lys Ala Ala Tyr Glu
        355                 360                 365

Lys Leu Val Asn Ala Ile Gly Thr Lys Tyr Lys Gly Arg Ala Lys Gly
    370                 375                 380

Val Val Lys Phe Ser Ala Pro Leu Ala His Met Leu Thr Ala Gly Ala
385                 390                 395                 400

Asp Phe Met Leu Val Pro Ser Arg Phe Glu Pro Cys Gly Leu Ile Gln
                405                 410                 415

Leu His Ala Met His Tyr Gly Thr Val Pro Val Val Ala Ser Thr Gly
            420                 425                 430

Gly Leu Val Asp Thr Val Lys Glu Gly Val Thr Gly Phe His Met Gly
        435                 440                 445

Ala Leu Asn Pro Asp Lys Leu Asp Glu Ala Asp Ala Asp Ala Leu Ala
    450                 455                 460

Ala Thr Val Arg Arg Ala Ser Glu Val Phe Ala Gly Gly Arg Tyr Pro
465                 470                 475                 480

Glu Met Val Ala Asn Cys Ile Ser Gln Asp Leu Ser Trp Ser Lys Pro
                485                 490                 495

Ala Gln Lys Trp Glu Gly Leu Leu Glu Glu Val Val Tyr Gly Lys Gly
            500                 505                 510
```

-continued

```
Gly Val Ala Thr Ala Lys Lys Glu Glu Ile Lys Val Pro Val Ala Glu
            515                 520                 525

Lys Ile Pro Gly Asp Leu Pro Ala Val Ser Tyr Ala Pro Asn Thr Leu
    530                 535                 540

Lys Pro Val Ser Ala Ser Val Glu Gly Asn Gly Ala Ala Ala Pro Lys
545                 550                 555                 560

Val Gly Thr Thr Ala Pro Ala Met Gly Ala Trp Arg Ala Thr Thr Pro
                565                 570                 575

Ser Gly Pro Ser Pro Ala Ala Ala Thr Pro Lys Val Thr Thr Tyr Lys
            580                 585                 590

Pro Ala Leu Pro Ala Thr Ala Lys Pro Lys Thr Ala Gly Leu Lys Leu
            595                 600                 605

Ala Gly Glu Ala Ser Thr Thr Ser Thr Ser Glu Asn Gly Ala Ala Ser
            610                 615                 620

Asn Gly Asn Gly Asn Gly Ala Ser Ala Ser Lys Thr Ser Ala Ala Lys
625                 630                 635                 640

Pro Leu Val Ser Ala Ala Thr Arg Lys Ser Ala
            645                 650
```

```
<210> SEQ ID NO 6
<211> LENGTH: 1314
<212> TYPE: DNA
<213> ORGANISM: Chlamydomonas reinhardtii
<220> FEATURE:
<223> OTHER INFORMATION: Fragment of the complete cDNA coding for the
      GBSSI of Chlamydomonas reinhardtii
<220> FEATURE:
<221> NAME/KEY: CDS
<222> LOCATION: (1)..(1314)

<400> SEQUENCE: 6
```

```
gcg ctg gac atc gtg atg gtt gct gct gag gtc gcc cct tgg tcc aag      48
Ala Leu Asp Ile Val Met Val Ala Ala Glu Val Ala Pro Trp Ser Lys
 1               5                  10                  15 acg ggc ggc ctg ggc gat gtg act ggt ggc ctg cct att gag ctg gtc      96
Thr Gly Gly Leu Gly Asp Val Thr Gly Gly Leu Pro Ile Glu Leu Val
             20                  25                  30 aag cgc ggc cac cgc gtc atg acc att gcc cct cgc tac gac cag tac     144
Lys Arg Gly His Arg Val Met Thr Ile Ala Pro Arg Tyr Asp Gln Tyr
         35                  40                  45 gct gac gcc tgg gac acc tcg gtg gtc gtg gac atc atg ggc gag aag     192
Ala Asp Ala Trp Asp Thr Ser Val Val Val Asp Ile Met Gly Glu Lys
     50                  55                  60 gtc cgc tac ttc cac tcc atc aag aag ggc gtg cac cgc gtg tgg att     240
Val Arg Tyr Phe His Ser Ile Lys Lys Gly Val His Arg Val Trp Ile
 65                  70                  75                  80 gac cac ccc tgg ttc ctg gcc aag gtc tgg ggc aag acc ggc tcc aag     288
Asp His Pro Trp Phe Leu Ala Lys Val Trp Gly Lys Thr Gly Ser Lys
                 85                  90                  95 ctg tac ggc ccc cgc tcc ggc gct gac tac ctg gac aac cac aag cgc     336
Leu Tyr Gly Pro Arg Ser Gly Ala Asp Tyr Leu Asp Asn His Lys Arg
            100                 105                 110 ttc gcc ctg ttc tgc aag gcc gct att gag gct gcc cgc gtg ctg ccc     384
Phe Ala Leu Phe Cys Lys Ala Ala Ile Glu Ala Ala Arg Val Leu Pro
        115                 120                 125 ttc ggc ccc ggc gag gac tgc gtc ttc gtg gcc aac gac tgg cac tcc     432
Phe Gly Pro Gly Glu Asp Cys Val Phe Val Ala Asn Asp Trp His Ser
    130                 135                 140 gcc ctg gtg ccc gtc ctg ctg aag gac gag tac cag ccc aag ggc cag     480
Ala Leu Val Pro Val Leu Leu Lys Asp Glu Tyr Gln Pro Lys Gly Gln
```

```
                145                 150                 155                 160
ttc acc aag gcc aag tcg gtg ctg gct atc cac aac atc gcc ttc cag        528
Phe Thr Lys Ala Lys Ser Val Leu Ala Ile His Asn Ile Ala Phe Gln
            165                 170                 175 ggc cgc atg tgg gag gag gct ttc aag gac acg aag ctg ccc cag gcc        576
Gly Arg Met Trp Glu Glu Ala Phe Lys Asp Thr Lys Leu Pro Gln Ala
        180                 185                 190 gcc ttt gac aag ctg gcc ttc tcg gac ggc tat gcc aag gtt tac act        624
Ala Phe Asp Lys Leu Ala Phe Ser Asp Gly Tyr Ala Lys Val Tyr Thr
    195                 200                 205 gag gcc acc ccc atg gag gag gac gag aag ccc ccg ctg acg gga aag        672
Glu Ala Thr Pro Met Glu Glu Asp Glu Lys Pro Pro Leu Thr Gly Lys
210                 215                 220 acc tac aag aag atc aac tgg ctg aag ggt ggc att atc gcc gcc gac        720
Thr Tyr Lys Lys Ile Asn Trp Leu Lys Gly Gly Ile Ile Ala Ala Asp
225                 230                 235                 240 aag ctg gtg act gtg tcg ccc aac tac gcg acc gag atc gct gcc gat        768
Lys Leu Val Thr Val Ser Pro Asn Tyr Ala Thr Glu Ile Ala Ala Asp
                245                 250                 255 gcc gcc ggc ggt gtg gag ctg gac acc gtc atc cgc gcc aag ggc att        816
Ala Ala Gly Gly Val Glu Leu Asp Thr Val Ile Arg Ala Lys Gly Ile
            260                 265                 270 gag ggc att gtg aac ggc atg gac att gag gag tgg aac ccc aag acc        864
Glu Gly Ile Val Asn Gly Met Asp Ile Glu Glu Trp Asn Pro Lys Thr
        275                 280                 285 gac aag ttc ctg tct gcg ccc tac gac cag aac agc gtc tac gcc ggc        912
Asp Lys Phe Leu Ser Ala Pro Tyr Asp Gln Asn Ser Val Tyr Ala Gly
    290                 295                 300 aag gcc gcc gcc aag gag gcc ctg cag gcc gag ctg ggc ctg cct gtg        960
Lys Ala Ala Ala Lys Glu Ala Leu Gln Ala Glu Leu Gly Leu Pro Val
305                 310                 315                 320 gac ccc acc gcc ccc ctg ttc gcc ttc atc ggc cgc ctg gag gag cag       1008
Asp Pro Thr Ala Pro Leu Phe Ala Phe Ile Gly Arg Leu Glu Glu Gln
                325                 330                 335 aag ggt gtg gac atc atc ctg gcc gcc ctg ccc aag atc ctg gcc acc       1056
Lys Gly Val Asp Ile Ile Leu Ala Ala Leu Pro Lys Ile Leu Ala Thr
            340                 345                 350 ccc aag gtg cag atc gcc atc ctg ggt acc ggc aag gcc gcc tac gag       1104
Pro Lys Val Gln Ile Ala Ile Leu Gly Thr Gly Lys Ala Ala Tyr Glu
        355                 360                 365 aag ctg gtg aac gcc atc ggc acc aag tac aag ggc cgc gcc aag ggc       1152
Lys Leu Val Asn Ala Ile Gly Thr Lys Tyr Lys Gly Arg Ala Lys Gly
    370                 375                 380 gtg gtc aag ttc tcg gcg ccc ctg gcg cac atg ctc acc gcc ggc gcc       1200
Val Val Lys Phe Ser Ala Pro Leu Ala His Met Leu Thr Ala Gly Ala
385                 390                 395                 400 gac ttc atg ctg gtg ccc tcg cgc ttc gag ccc tgc ggc ctg atc cag       1248
Asp Phe Met Leu Val Pro Ser Arg Phe Glu Pro Cys Gly Leu Ile Gln
                405                 410                 415 ctg cac gcc atg cac tac ggt acc gtg ccc gtg gta gcc tcc acc ggc       1296
Leu His Ala Met His Tyr Gly Thr Val Pro Val Val Ala Ser Thr Gly
            420                 425                 430 ggc ctg gtc gac acc gtc                                                1314
Gly Leu Val Asp Thr Val
        435

<210> SEQ ID NO 7
<211> LENGTH: 438
<212> TYPE: PRT
<213> ORGANISM: Chlamydomonas reinhardtii
```

-continued

<400> SEQUENCE: 7

```
Ala Leu Asp Ile Val Met Val Ala Glu Val Ala Pro Trp Ser Lys
 1               5                  10                  15

Thr Gly Gly Leu Gly Asp Val Thr Gly Leu Pro Ile Glu Leu Val
            20                  25                  30

Lys Arg Gly His Arg Val Met Thr Ile Ala Pro Arg Tyr Asp Gln Tyr
        35                  40                  45

Ala Asp Ala Trp Asp Thr Ser Val Val Asp Ile Met Gly Glu Lys
    50                  55                  60

Val Arg Tyr Phe His Ser Ile Lys Lys Gly Val His Arg Val Trp Ile
 65                  70                  75                  80

Asp His Pro Trp Phe Leu Ala Lys Val Trp Gly Lys Thr Gly Ser Lys
                85                  90                  95

Leu Tyr Gly Pro Arg Ser Gly Ala Asp Tyr Leu Asp Asn His Lys Arg
            100                 105                 110

Phe Ala Leu Phe Cys Lys Ala Ala Ile Glu Ala Ala Arg Val Leu Pro
        115                 120                 125

Phe Gly Pro Gly Glu Asp Cys Val Phe Val Ala Asn Asp Trp His Ser
    130                 135                 140

Ala Leu Val Pro Val Leu Leu Lys Asp Glu Tyr Gln Pro Lys Gly Gln
145                 150                 155                 160

Phe Thr Lys Ala Lys Ser Val Leu Ala Ile His Asn Ile Ala Phe Gln
                165                 170                 175

Gly Arg Met Trp Glu Glu Ala Phe Lys Asp Thr Lys Leu Pro Gln Ala
            180                 185                 190

Ala Phe Asp Lys Leu Ala Phe Ser Asp Gly Tyr Ala Lys Val Tyr Thr
        195                 200                 205

Glu Ala Thr Pro Met Glu Glu Asp Glu Lys Pro Pro Leu Thr Gly Lys
    210                 215                 220

Thr Tyr Lys Lys Ile Asn Trp Leu Lys Gly Gly Ile Ile Ala Ala Asp
225                 230                 235                 240

Lys Leu Val Thr Val Ser Pro Asn Tyr Ala Thr Glu Ile Ala Ala Asp
                245                 250                 255

Ala Ala Gly Gly Val Glu Leu Asp Thr Val Ile Arg Ala Lys Gly Ile
            260                 265                 270

Glu Gly Ile Val Asn Gly Met Asp Ile Glu Glu Trp Asn Pro Lys Thr
        275                 280                 285

Asp Lys Phe Leu Ser Ala Pro Tyr Asp Gln Asn Ser Val Tyr Ala Gly
    290                 295                 300

Lys Ala Ala Lys Glu Ala Leu Gln Ala Glu Leu Gly Leu Pro Val
305                 310                 315                 320

Asp Pro Thr Ala Pro Leu Phe Ala Phe Ile Gly Arg Leu Glu Glu Gln
                325                 330                 335

Lys Gly Val Asp Ile Ile Leu Ala Ala Leu Pro Lys Ile Leu Ala Thr
            340                 345                 350

Pro Lys Val Gln Ile Ala Ile Leu Gly Thr Gly Lys Ala Ala Tyr Glu
        355                 360                 365

Lys Leu Val Asn Ala Ile Gly Thr Lys Tyr Lys Gly Arg Ala Lys Gly
    370                 375                 380

Val Val Lys Phe Ser Ala Pro Leu Ala His Met Leu Thr Ala Gly Ala
385                 390                 395                 400

Asp Phe Met Leu Val Pro Ser Arg Phe Glu Pro Cys Gly Leu Ile Gln
```

-continued

```
                    405                 410                 415
Leu His Ala Met His Tyr Gly Thr Val Pro Val Val Ala Ser Thr Gly
            420                 425                 430

Gly Leu Val Asp Thr Val
        435
```

<210> SEQ ID NO 8
<211> LENGTH: 1593
<212> TYPE: DNA
<213> ORGANISM: Chlamydomonas reinhardtii
<220> FEATURE:
<223> OTHER INFORMATION: Fragment of the complete cDNA coding for the
       GBSSI of Chlamydomonas reinhardtii
<220> FEATURE:
<221> NAME/KEY: CDS
<222> LOCATION: (1)..(1593)

<400> SEQUENCE: 8

```
gcg ctg gac atc gtg atg gtt gct gct gag gtc gcc cct tgg tcc aag      48
Ala Leu Asp Ile Val Met Val Ala Ala Glu Val Ala Pro Trp Ser Lys
 1               5                  10                  15 acg ggc ggc ctg ggc gat gtg act ggt ggc ctg cct att gag ctg gtc      96
Thr Gly Gly Leu Gly Asp Val Thr Gly Gly Leu Pro Ile Glu Leu Val
            20                  25                  30 aag cgc ggc cac cgc gtc atg acc att gcc cct cgc tac gac cag tac     144
Lys Arg Gly His Arg Val Met Thr Ile Ala Pro Arg Tyr Asp Gln Tyr
        35                  40                  45 gct gac gcc tgg gac acc tcg gtg gtc gtg gac atc atg ggc gag aag     192
Ala Asp Ala Trp Asp Thr Ser Val Val Val Asp Ile Met Gly Glu Lys
    50                  55                  60 gtc cgc tac ttc cac tcc atc aag aag ggc gtg cac cgc gtg tgg att     240
Val Arg Tyr Phe His Ser Ile Lys Lys Gly Val His Arg Val Trp Ile
 65                  70                  75                  80 gac cac ccc tgg ttc ctg gcc aag gtc tgg ggc aag acc ggc tcc aag     288
Asp His Pro Trp Phe Leu Ala Lys Val Trp Gly Lys Thr Gly Ser Lys
                85                  90                  95 ctg tac ggc ccc cgc tcc ggc gct gac tac ctg gac aac cac aag cgc     336
Leu Tyr Gly Pro Arg Ser Gly Ala Asp Tyr Leu Asp Asn His Lys Arg
            100                 105                 110 ttc gcc ctg ttc tgc aag gcc gct att gag gct gcc cgc gtg ctg ccc     384
Phe Ala Leu Phe Cys Lys Ala Ala Ile Glu Ala Ala Arg Val Leu Pro
        115                 120                 125 ttc ggc ccc ggc gag gac tgc gtc ttc gtg gcc aac gac tgg cac tcc     432
Phe Gly Pro Gly Glu Asp Cys Val Phe Val Ala Asn Asp Trp His Ser
    130                 135                 140 gcc ctg gtg ccc gtc ctg ctg aag gac gag tac cag ccc aag ggc cag     480
Ala Leu Val Pro Val Leu Leu Lys Asp Glu Tyr Gln Pro Lys Gly Gln
145                 150                 155                 160 ttc acc aag gcc aag tcg gtg ctg gct atc cac aac atc gcc ttc cag     528
Phe Thr Lys Ala Lys Ser Val Leu Ala Ile His Asn Ile Ala Phe Gln
                165                 170                 175 ggc cgc atg tgg gag gag gct ttc aag gac acg aag ctg ccc cag gcc     576
Gly Arg Met Trp Glu Glu Ala Phe Lys Asp Thr Lys Leu Pro Gln Ala
            180                 185                 190 gcc ttt gac aag ctg gcc ttc tcg gac ggc tat gcc aag gtt tac act     624
Ala Phe Asp Lys Leu Ala Phe Ser Asp Gly Tyr Ala Lys Val Tyr Thr
        195                 200                 205 gag gcc acc ccc atg gag gag gac gag aag ccc ccg ctg acg gga aag     672
Glu Ala Thr Pro Met Glu Glu Asp Glu Lys Pro Pro Leu Thr Gly Lys
    210                 215                 220 acc tac aag aag atc aac tgg ctg aag ggt ggc att atc gcc gcc gac     720
```

```
Thr Tyr Lys Lys Ile Asn Trp Leu Lys Gly Gly Ile Ala Ala Asp
225                 230                 235                 240 aag ctg gtg act gtg tcg ccc aac tac gcg acc gag atc gct gcc gat        768
Lys Leu Val Thr Val Ser Pro Asn Tyr Ala Thr Glu Ile Ala Ala Asp
                    245                 250                 255 gcc gcc ggc ggt gtg gag ctg gac acc gtc atc cgc gcc aag ggc att        816
Ala Ala Gly Gly Val Glu Leu Asp Thr Val Ile Arg Ala Lys Gly Ile
                260                 265                 270 gag ggc att gtg aac ggc atg gac att gag gag tgg aac ccc aag acc        864
Glu Gly Ile Val Asn Gly Met Asp Ile Glu Glu Trp Asn Pro Lys Thr
            275                 280                 285 gac aag ttc ctg tct gcg ccc tac gac cag aac agc gtc tac gcc ggc        912
Asp Lys Phe Leu Ser Ala Pro Tyr Asp Gln Asn Ser Val Tyr Ala Gly
        290                 295                 300 aag gcc gcc gcc aag gag gcc ctg cag gcc gag ctg ggc ctg cct gtg        960
Lys Ala Ala Ala Lys Glu Ala Leu Gln Ala Glu Leu Gly Leu Pro Val
305                 310                 315                 320 gac ccc acc gcc ccc ctg ttc gcc ttc atc ggc cgc ctg gag gag cag       1008
Asp Pro Thr Ala Pro Leu Phe Ala Phe Ile Gly Arg Leu Glu Glu Gln
                    325                 330                 335 aag ggt gtg gac atc atc ctg gcc gcc ctg ccc aag atc ctg gcc acc       1056
Lys Gly Val Asp Ile Ile Leu Ala Ala Leu Pro Lys Ile Leu Ala Thr
                340                 345                 350 ccc aag gtg cag atc gcc atc ctg ggt acc ggc aag gcc gcc tac gag       1104
Pro Lys Val Gln Ile Ala Ile Leu Gly Thr Gly Lys Ala Ala Tyr Glu
            355                 360                 365 aag ctg gtg aac gcc atc ggc acc aag tac aag ggc cgc gcc aag ggc       1152
Lys Leu Val Asn Ala Ile Gly Thr Lys Tyr Lys Gly Arg Ala Lys Gly
        370                 375                 380 gtg gtc aag ttc tcg gcg ccc ctg gcg cac atg ctc acc gcc ggc gcc       1200
Val Val Lys Phe Ser Ala Pro Leu Ala His Met Leu Thr Ala Gly Ala
385                 390                 395                 400 gac ttc atg ctg gtg ccc tcg cgc ttc gag ccc tgc ggc ctg atc cag       1248
Asp Phe Met Leu Val Pro Ser Arg Phe Glu Pro Cys Gly Leu Ile Gln
                    405                 410                 415 ctg cac gcc atg cac tac ggt acc gtg ccc gtg gta gcc tcc acc ggc       1296
Leu His Ala Met His Tyr Gly Thr Val Pro Val Val Ala Ser Thr Gly
                420                 425                 430 ggc ctg gtc gac acc gtc aag gag ggc gtc acc ggc ttc cac atg ggc       1344
Gly Leu Val Asp Thr Val Lys Glu Gly Val Thr Gly Phe His Met Gly
            435                 440                 445 gcc ctg aac ccc gac aag ctg gac gag gct gac gcc gac gcc ctg gcc       1392
Ala Leu Asn Pro Asp Lys Leu Asp Glu Ala Asp Ala Asp Ala Leu Ala
        450                 455                 460 gcc acc gtg cgc cgt gcc agc gag gtg ttt gcg ggc ggc cgc tac ccc       1440
Ala Thr Val Arg Arg Ala Ser Glu Val Phe Ala Gly Gly Arg Tyr Pro
465                 470                 475                 480 gag atg gtg gcc aac tgc atc agc cag gac ctg tcc tgg tcc aag ccc       1488
Glu Met Val Ala Asn Cys Ile Ser Gln Asp Leu Ser Trp Ser Lys Pro
                    485                 490                 495 gcc cag aag tgg gag ggc ctg ctg gag gag gtg gtg tac ggc aag ggc       1536
Ala Gln Lys Trp Glu Gly Leu Leu Glu Glu Val Val Tyr Gly Lys Gly
                500                 505                 510 ggc gtg gcc acc gcc aag aag gag gag atc aag gtg ccc gtt gcc gag       1584
Gly Val Ala Thr Ala Lys Lys Glu Glu Ile Lys Val Pro Val Ala Glu
            515                 520                 525 aag atc ccc                                                           1593
Lys Ile Pro
        530
```

```
<210> SEQ ID NO 9
<211> LENGTH: 531
<212> TYPE: PRT
<213> ORGANISM: Chlamydomonas reinhardtii

<400> SEQUENCE: 9
```

| | | | | | | | | | | | | | | | |
|---|---|---|---|---|---|---|---|---|---|---|---|---|---|---|---|
| Ala | Leu | Asp | Ile | Val | Met | Val | Ala | Ala | Glu | Val | Ala | Pro | Trp | Ser | Lys |
| 1 | | | | 5 | | | | | 10 | | | | | 15 | |

| | | | | | | | | | | | | | | | |
|---|---|---|---|---|---|---|---|---|---|---|---|---|---|---|---|
| Thr | Gly | Gly | Leu | Gly | Asp | Val | Thr | Gly | Gly | Leu | Pro | Ile | Glu | Leu | Val |
| | | | | 20 | | | | | 25 | | | | | 30 | |

| | | | | | | | | | | | | | | | |
|---|---|---|---|---|---|---|---|---|---|---|---|---|---|---|---|
| Lys | Arg | Gly | His | Arg | Val | Met | Thr | Ile | Ala | Pro | Arg | Tyr | Asp | Gln | Tyr |
| | | | 35 | | | | | 40 | | | | | 45 | | |

| | | | | | | | | | | | | | | | |
|---|---|---|---|---|---|---|---|---|---|---|---|---|---|---|---|
| Ala | Asp | Ala | Trp | Asp | Thr | Ser | Val | Val | Asp | Ile | Met | Gly | Glu | Lys |
| | 50 | | | | | 55 | | | | | 60 | | | | |

| | | | | | | | | | | | | | | | |
|---|---|---|---|---|---|---|---|---|---|---|---|---|---|---|---|
| Val | Arg | Tyr | Phe | His | Ser | Ile | Lys | Lys | Gly | Val | His | Arg | Val | Trp | Ile |
| 65 | | | | | 70 | | | | | 75 | | | | | 80 |

| | | | | | | | | | | | | | | | |
|---|---|---|---|---|---|---|---|---|---|---|---|---|---|---|---|
| Asp | His | Pro | Trp | Phe | Leu | Ala | Lys | Val | Trp | Gly | Lys | Thr | Gly | Ser | Lys |
| | | | | 85 | | | | | 90 | | | | | 95 | |

| | | | | | | | | | | | | | | | |
|---|---|---|---|---|---|---|---|---|---|---|---|---|---|---|---|
| Leu | Tyr | Gly | Pro | Arg | Ser | Gly | Ala | Asp | Tyr | Leu | Asp | Asn | His | Lys | Arg |
| | | | 100 | | | | | 105 | | | | | 110 | | |

| | | | | | | | | | | | | | | | |
|---|---|---|---|---|---|---|---|---|---|---|---|---|---|---|---|
| Phe | Ala | Leu | Phe | Cys | Lys | Ala | Ala | Ile | Glu | Ala | Ala | Arg | Val | Leu | Pro |
| | | 115 | | | | | 120 | | | | | 125 | | | |

| | | | | | | | | | | | | | | | |
|---|---|---|---|---|---|---|---|---|---|---|---|---|---|---|---|
| Phe | Gly | Pro | Gly | Glu | Asp | Cys | Val | Phe | Val | Ala | Asn | Asp | Trp | His | Ser |
| | 130 | | | | | 135 | | | | | 140 | | | | |

| | | | | | | | | | | | | | | | |
|---|---|---|---|---|---|---|---|---|---|---|---|---|---|---|---|
| Ala | Leu | Val | Pro | Val | Leu | Leu | Lys | Asp | Glu | Tyr | Gln | Pro | Lys | Gly | Gln |
| 145 | | | | | 150 | | | | | 155 | | | | | 160 |

| | | | | | | | | | | | | | | | |
|---|---|---|---|---|---|---|---|---|---|---|---|---|---|---|---|
| Phe | Thr | Lys | Ala | Lys | Ser | Val | Leu | Ala | Ile | His | Asn | Ile | Ala | Phe | Gln |
| | | | | 165 | | | | | 170 | | | | | 175 | |

| | | | | | | | | | | | | | | | |
|---|---|---|---|---|---|---|---|---|---|---|---|---|---|---|---|
| Gly | Arg | Met | Trp | Glu | Glu | Ala | Phe | Lys | Asp | Thr | Lys | Leu | Pro | Gln | Ala |
| | | | 180 | | | | | 185 | | | | | 190 | | |

| | | | | | | | | | | | | | | | |
|---|---|---|---|---|---|---|---|---|---|---|---|---|---|---|---|
| Ala | Phe | Asp | Lys | Leu | Ala | Phe | Ser | Asp | Gly | Tyr | Ala | Lys | Val | Tyr | Thr |
| | | 195 | | | | | 200 | | | | | 205 | | | |

| | | | | | | | | | | | | | | | |
|---|---|---|---|---|---|---|---|---|---|---|---|---|---|---|---|
| Glu | Ala | Thr | Pro | Met | Glu | Glu | Asp | Glu | Lys | Pro | Pro | Leu | Thr | Gly | Lys |
| | 210 | | | | | 215 | | | | | 220 | | | | |

| | | | | | | | | | | | | | | | |
|---|---|---|---|---|---|---|---|---|---|---|---|---|---|---|---|
| Thr | Tyr | Lys | Lys | Ile | Asn | Trp | Leu | Lys | Gly | Gly | Ile | Ile | Ala | Ala | Asp |
| 225 | | | | | 230 | | | | | 235 | | | | | 240 |

| | | | | | | | | | | | | | | | |
|---|---|---|---|---|---|---|---|---|---|---|---|---|---|---|---|
| Lys | Leu | Val | Thr | Val | Ser | Pro | Asn | Tyr | Ala | Thr | Glu | Ile | Ala | Ala | Asp |
| | | | | 245 | | | | | 250 | | | | | 255 | |

| | | | | | | | | | | | | | | | |
|---|---|---|---|---|---|---|---|---|---|---|---|---|---|---|---|
| Ala | Ala | Gly | Gly | Val | Glu | Leu | Asp | Thr | Val | Ile | Arg | Ala | Lys | Gly | Ile |
| | | | 260 | | | | | 265 | | | | | 270 | | |

| | | | | | | | | | | | | | | | |
|---|---|---|---|---|---|---|---|---|---|---|---|---|---|---|---|
| Glu | Gly | Ile | Val | Asn | Gly | Met | Asp | Ile | Glu | Glu | Trp | Asn | Pro | Lys | Thr |
| | | 275 | | | | | 280 | | | | | 285 | | | |

| | | | | | | | | | | | | | | | |
|---|---|---|---|---|---|---|---|---|---|---|---|---|---|---|---|
| Asp | Lys | Phe | Leu | Ser | Ala | Pro | Tyr | Asp | Gln | Asn | Ser | Val | Tyr | Ala | Gly |
| | 290 | | | | | 295 | | | | | 300 | | | | |

| | | | | | | | | | | | | | | | |
|---|---|---|---|---|---|---|---|---|---|---|---|---|---|---|---|
| Lys | Ala | Ala | Ala | Lys | Glu | Ala | Leu | Gln | Ala | Glu | Leu | Gly | Leu | Pro | Val |
| 305 | | | | | 310 | | | | | 315 | | | | | 320 |

| | | | | | | | | | | | | | | | |
|---|---|---|---|---|---|---|---|---|---|---|---|---|---|---|---|
| Asp | Pro | Thr | Ala | Pro | Leu | Phe | Ala | Phe | Ile | Gly | Arg | Leu | Glu | Glu | Gln |
| | | | | 325 | | | | | 330 | | | | | 335 | |

| | | | | | | | | | | | | | | | |
|---|---|---|---|---|---|---|---|---|---|---|---|---|---|---|---|
| Lys | Gly | Val | Asp | Ile | Ile | Leu | Ala | Ala | Leu | Pro | Lys | Ile | Leu | Ala | Thr |
| | | | 340 | | | | | 345 | | | | | 350 | | |

| | | | | | | | | | | | | | | | |
|---|---|---|---|---|---|---|---|---|---|---|---|---|---|---|---|
| Pro | Lys | Val | Gln | Ile | Ala | Ile | Leu | Gly | Thr | Gly | Lys | Ala | Ala | Tyr | Glu |
| | | 355 | | | | | 360 | | | | | 365 | | | |

| | | | | | | | | | | | | | | | |
|---|---|---|---|---|---|---|---|---|---|---|---|---|---|---|---|
| Lys | Leu | Val | Asn | Ala | Ile | Gly | Thr | Lys | Tyr | Lys | Gly | Arg | Ala | Lys | Gly |
| | 370 | | | | | 375 | | | | | 380 | | | | |

```
Val Val Lys Phe Ser Ala Pro Leu Ala His Met Leu Thr Ala Gly Ala
385                 390                 395                 400

Asp Phe Met Leu Val Pro Ser Arg Phe Glu Pro Cys Gly Leu Ile Gln
                405                 410                 415

Leu His Ala Met His Tyr Gly Thr Val Pro Val Val Ala Ser Thr Gly
                420                 425                 430

Gly Leu Val Asp Thr Val Lys Glu Gly Val Thr Gly Phe His Met Gly
            435                 440                 445

Ala Leu Asn Pro Asp Lys Leu Asp Glu Ala Asp Ala Asp Leu Ala
        450                 455                 460

Ala Thr Val Arg Arg Ala Ser Glu Val Phe Ala Gly Arg Tyr Pro
465                 470                 475                 480

Glu Met Val Ala Asn Cys Ile Ser Gln Asp Leu Ser Trp Ser Lys Pro
                485                 490                 495

Ala Gln Lys Trp Glu Gly Leu Leu Glu Glu Val Val Tyr Gly Lys Gly
            500                 505                 510

Gly Val Ala Thr Ala Lys Lys Glu Glu Ile Lys Val Pro Val Ala Glu
            515                 520                 525

Lys Ile Pro
        530

<210> SEQ ID NO 10
<211> LENGTH: 1696
<212> TYPE: DNA
<213> ORGANISM: Chlamydomonas reinhardtii
<220> FEATURE:
<223> OTHER INFORMATION: cDNA coding for the carboxy terminal sequence
      for the GBSSI of Chlamydomonas reinhardtii
<220> FEATURE:
<221> NAME/KEY: CDS
<222> LOCATION: (3)..(716)

<400> SEQUENCE: 10 at tcg gca cga gtg cac gcc atg cac tac ggt acc gtg ccc gtg gta        47
   Ser Ala Arg Val His Ala Met His Tyr Gly Thr Val Pro Val Val
   1               5                   10                  15 gcc tcc acc ggc ggc ctg gtc gac acc gtc aag gag ggc gtc acc ggc        95
Ala Ser Thr Gly Gly Leu Val Asp Thr Val Lys Glu Gly Val Thr Gly
                20                  25                  30 ttc cac atg ggc gcc ctg aac ccc gac aag ctg gac gag gct gac gcc       143
Phe His Met Gly Ala Leu Asn Pro Asp Lys Leu Asp Glu Ala Asp Ala
            35                  40                  45 gac gcc ctg gcc gcc acc gtg cgc cgt gcc agc gag gtg ttt gcg ggc       191
Asp Ala Leu Ala Ala Thr Val Arg Arg Ala Ser Glu Val Phe Ala Gly
        50                  55                  60 ggc cgc tac ccc gag atg gtg gcc aac tgc atc agc cag gac ctg tcc       239
Gly Arg Tyr Pro Glu Met Val Ala Asn Cys Ile Ser Gln Asp Leu Ser
65                  70                  75                  80 tgg tcc aag ccc gcc cag aag tgg gag ggc ctg ctg gag gag gtg gtg       287
Trp Ser Lys Pro Ala Gln Lys Trp Glu Gly Leu Leu Glu Glu Val Val
                85                  90                  95 tac ggc aag ggc ggc gtg gcc acc gcc aag aag gag gag atc aag gtg       335
Tyr Gly Lys Gly Gly Val Ala Thr Ala Lys Lys Glu Glu Ile Lys Val
            100                 105                 110 ccc gtt gcc gag aag atc ccc ggc gac ctg ccc gcc gtg tcc tac gcc       383
Pro Val Ala Glu Lys Ile Pro Gly Asp Leu Pro Ala Val Ser Tyr Ala
        115                 120                 125 ccc aac acc ctg aag ccc gtg tcc gcc tcc gtg gag ggc aac ggc gcc       431
Pro Asn Thr Leu Lys Pro Val Ser Ala Ser Val Glu Gly Asn Gly Ala
```

```
                    130             135             140
gcc gcg ccc aag gtc ggc acc acc gcc ccc gcc atg ggc gcg tgg cgc    479
Ala Ala Pro Lys Val Gly Thr Thr Ala Pro Ala Met Gly Ala Trp Arg
    145                 150                 155 gcg acc acc ccc tcg ggc ccc tcg ccc gcc gcc acc ccc aag gtg        527
Ala Thr Thr Pro Ser Gly Pro Ser Pro Ala Ala Thr Pro Lys Val
160                 165                 170                 175 acc acc tac aag ccc gcc ctg ccc gcc acc gcc aag ccc aag acc gct    575
Thr Thr Tyr Lys Pro Ala Leu Pro Ala Thr Ala Lys Pro Lys Thr Ala
                180                 185                 190 ggc ctc aag ctg gcc ggt gag gcc tcc acc acc tcg acc tcg gag aac    623
Gly Leu Lys Leu Ala Gly Glu Ala Ser Thr Thr Ser Thr Ser Glu Asn
        195                 200                 205 ggc gct gcc tcc aac ggc aac ggc aac ggt gcc tcg gcc tcc aag acc    671
Gly Ala Ala Ser Asn Gly Asn Gly Asn Gly Ala Ser Ala Ser Lys Thr
            210                 215                 220 tcg gct gcc aag ccc ctg gtc tcc gcc gcc acc cgc aag tcc gcc        716
Ser Ala Ala Lys Pro Leu Val Ser Ala Ala Thr Arg Lys Ser Ala
        225                 230                 235 taaagcggca gtagccgcag aggcggcgac agcatgagcg gctcgaccaa agctgtggca    776
ggaacggctg tagcagcggc aggcggccgc caccggcgag gagcaggctt gcggcagcga    836
gggcgatgag cttagcggcc gtgagcatgg caggcggaaa cgtgtgtact gaaatgtggt    896
gcatgagagt gtcgtgctgt aatgaagtcg gttttgcgag accggagaaa cgccggtttg    956
gttttgtagt gcagggcctg tggtttcggt tttgcccaag tccaaaagaa gagtaacgaa    1016
actgtagcag tagcagagca cttgcgcggc gcggcgacca cgccggcccg tgcgcagcct    1076
gtcctgccct cagccttgtg attcggcggc aagagggcgg gtctgtacac tccatccatt    1136
ccaggatttt tgcaggctgc ctgagagttt gccattttgt gggacgtgag cggcgggacg    1196
gccgcgccgg gctctcctac cgcctccggc aacggagaag tgggaggcgc tgtagcccgg    1256
tgacccccca atgtagagga tgggatacat aagagcgtgt ggaatggtgg taaaagagga    1316
ggggcctggg tcgcccctcg atggttttgt tgaggtgcag acggcaccgt cggcgtcaaa    1376
ggccctcgca aggcccgggt gccttgggct cattttggt gcccgtcgat gatgagagat    1436
tggccagcgg ttttttgagg ctggctcgaa gcgagggttt gtggaagtgg agcgaggagg    1496
gttggagaaa gaggcggaca tgcttgactg gaggtacaca aagtggagcg tgcgacggca    1556
cggaggcatt ggcggactat tgacccagta gtgtggaaag tagttggacc tgaattcttt    1616
gagagtaccg cgcattaatc cgtgagagag taacaaagat ggcacctgaa aaaaaaaaa    1676 aaaaaaaaaa aaaaaaaaaa                                               1696
```

<210> SEQ ID NO 11
<211> LENGTH: 1696
<212> TYPE: DNA
<213> ORGANISM: Chlamydomonas reinhardtii
<220> FEATURE:
<223> OTHER INFORMATION: cDNA coding for the carboxy terminal sequence for the GBSSI of Chlamydomonas reinhardtii

<400> SEQUENCE: 11

```
tttttttttt tttttttttt tttttttttt ttcaggtgcc atctttgtta ctctctcacg     60
gattaatgcg cggtactctc aaagaattca ggtccaacta ctttccacac tactgggtca    120
atagtccgcc aatgcctccg tgccgtcgca cgctccactt tgtgtacctc cagtcaagca    180
tgtccgcctc tttctccaac cctcctcgct ccacttccac aaaccctcgc ttcgagccag    240
```

```
cctcaaaaaa ccgctggcca atctctcatc atcgacgggc accaaaaatg agcccaaggc    300
acccgggcct tgcgagggcc tttgacgccg acggtgccgt ctgcacctca acaaaaccat    360
cgagggcgcga cccaggcccc tcctctttta ccaccattcc acacgctctt atgtatccca    420
tcctctacat tgggggtca ccgggctaca gcgcctccca cttctccgtt gccggaggcg    480
gtaggagagc ccggcgcggc cgtcccgccg ctcacgtccc acaaaatggc aaactctcag    540
gcagcctgca aaatcctgg aatggatgga gtgtacagac ccgccctctt gccgccgaat    600
cacaaggctg agggcaggac aggctgcgca cgggccggcg tggtcgccgc gccgcgcaag    660
tgctctgcta ctgctacagt ttcgttactc ttcttttgga cttgggcaaa accgaaacca    720
caggccctgc actacaaaac caaaccggcg tttctccggt ctcgcaaaac cgacttcatt    780
acagcacgac actctcatgc accacatttc agtacacacg tttccgcctg ccatgctcac    840
ggccgctaag ctcatcgccc tcgctgccgc aagcctgctc ctcgccggtg cggccgcct    900
gccgctgcta cagccgttcc tgccacagct ttggtcgagc cgctcatgct gtcgccgcct    960
ctgcggctac tgccgcttta ggcggacttg cgggtggcgg cggagaccag gggcttggca   1020
gccgaggtct tggaggccga ggcaccgttg ccgttgccgt tggaggcagc gccgttctcc   1080
gaggtcgagg tggtggaggc ctcaccggcc agcttgaggc cagcggtctt gggcttggcg   1140
gtggcgggca gggcgggctt gtaggtggtc accttggggg tggcggcggc gggcgagggg   1200
cccgaggggg tggtcgcgcg ccacgcgccc atggcggggg cggtggtgcc gaccttgggc   1260
gcggcggcgc cgttgccctc cacggaggcg gacacgggct tcagggtgtt gggggcgtag   1320
gacacggcgg gcaggtcgcc ggggatcttc tcggcaacgg gcaccttgat ctcctccttc   1380
ttggcggtgg ccacgccgcc cttgccgtac accacctcct ccagcaggcc ctcccacttc   1440
tgggcgggct tggaccagga caggtcctgg ctgatgcagt tggccaccat ctcggggtag   1500
cggccgcccg caaacacctc gctggcacgg cgcacggtgg cggccaggcc gtcggcgtca   1560
gcctcgtcca gcttgtcggg gttcagggcg cccatgtgga agccggtgac gccctccttg   1620
acggtgtcga ccaggccgcc ggtggaggct accacgggca cggtaccgta gtgcatggcg   1680
tgcactcgtg ccgaat                                                   1696
```

<210> SEQ ID NO 12
<211> LENGTH: 238
<212> TYPE: PRT
<213> ORGANISM: Chlamydomonas reinhardtii
<220> FEATURE:
<223> OTHER INFORMATION: Carboxy terminal peptide sequence of the GBSSI
    of Chlamydomonas reinhardtii <400> SEQUENCE: 12

Ser Ala Arg Val His Ala Met His Tyr Gly Thr Val Pro Val Val Ala
 1               5                  10                  15

Ser Thr Gly Gly Leu Val Asp Thr Val Lys Glu Gly Val Thr Gly Phe
                20                  25                  30

His Met Gly Ala Leu Asn Pro Asp Lys Leu Asp Glu Ala Asp Ala Asp
            35                  40                  45

Ala Leu Ala Ala Thr Val Arg Arg Ala Ser Glu Val Phe Ala Gly Gly
        50                  55                  60

Arg Tyr Pro Glu Met Val Ala Asn Cys Ile Ser Gln Asp Leu Ser Trp
 65                  70                  75                  80

Ser Lys Pro Ala Gln Lys Trp Glu Gly Leu Leu Glu Glu Val Val Tyr
                85                  90                  95

```
Gly Lys Gly Gly Val Ala Thr Ala Lys Lys Glu Ile Lys Val Pro
            100                 105                 110

Val Ala Glu Lys Ile Pro Gly Asp Leu Pro Ala Val Ser Tyr Ala Pro
        115                 120                 125

Asn Thr Leu Lys Pro Val Ser Ala Ser Val Glu Gly Asn Gly Ala Ala
    130                 135                 140

Ala Pro Lys Val Gly Thr Thr Ala Pro Ala Met Gly Ala Trp Arg Ala
145                 150                 155                 160

Thr Thr Pro Ser Gly Pro Ser Pro Ala Ala Thr Pro Lys Val Thr
                165                 170                 175

Thr Tyr Lys Pro Ala Leu Pro Ala Thr Ala Lys Pro Lys Thr Ala Gly
            180                 185                 190

Leu Lys Leu Ala Gly Glu Ala Ser Thr Thr Ser Thr Ser Glu Asn Gly
        195                 200                 205

Ala Ala Ser Asn Gly Asn Gly Asn Gly Ala Ser Ala Ser Lys Thr Ser
    210                 215                 220

Ala Ala Lys Pro Leu Val Ser Ala Ala Thr Arg Lys Ser Ala
225                 230                 235
```

```
<210> SEQ ID NO 13
<211> LENGTH: 23
<212> TYPE: PRT
<213> ORGANISM: Chlamydomonas reinhardtii
<220> FEATURE:
<223> OTHER INFORMATION: Amino terminal fragment of GBSSI of
      Chlamydomonas reinhardtii

<400> SEQUENCE: 13

Ala Leu Asp Ile Val Met Val Ala Ala Glu Val Ala Pro Gly Gly Lys
  1               5                  10                  15

Thr Gly Gly Leu Gly Asp Val
             20
```

```
<210> SEQ ID NO 14
<211> LENGTH: 23
<212> TYPE: PRT
<213> ORGANISM: Chlamydomonas reinhardtii
<220> FEATURE:
<223> OTHER INFORMATION: Amino terminal fragment of GBSSI of
      Chlamydomonas reinhardtii

<400> SEQUENCE: 14

Ala Leu Asp Ile Val Met Val Ala Ala Glu Val Ala Pro Trp Ser Lys
  1               5                  10                  15

Thr Gly Gly Leu Gly Asp Val
             20
```

```
<210> SEQ ID NO 15
<211> LENGTH: 3117
<212> TYPE: DNA
<213> ORGANISM: Chlamydomonas reinhardtii

<400> SEQUENCE: 15
tttttttttt tttttttttt tttttttttt tcaggtgcca tctttgttac tctctcacgg      60
attaatgcgc ggtactctca aagaattcag gtccaactac tttccacact actgggtcaa    120
tagtccgcca atgcctccgt gccgtcgcac gctccacttt gtgtacctcc agtcaagcat    180
gtccgcctct ttctccaacc ctcctcgctc cacttccaca aaccctcgct tcgagccagc    240
ctcaaaaaac cgctggccaa tctctcatca tcgacgggca ccaaaaatga gcccaaggca    300
```

-continued

```
cccgggcctt gcgagggcct ttgacgccga cggtgccgtc tgcacctcaa caaaaccatc      360
gaggggcgac ccaggcccct cctcttttac caccattcca cacgctctta tgtatcccat      420
cctctacatt gggggtcac cgggctacag cgcctcccac ttctccgttg ccggaggcgg       480
taggagagcc cggcgcggcc gtcccgccgc tcacgtccca caaaatggca aactctcagg      540
cagcctgcaa aaatcctgga atggatggag tgtacagacc cgccctcttg ccgccgaatc      600
acaaggctga gggcaggaca ggctgcgcac gggccggcgt ggtcgccgcg ccgcgcaagt      660
gctctgctac tgctacagtt tcgttactct tcttttggac ttgggcaaaa ccgaaaccac      720
aggccctgca ctacaaaacc aaaccggcgt ttctccggtc tcgcaaaacc gacttcatta      780
cagcacgaca ctctcatgca ccacatttca gtacacacgt ttccgcctgc catgctcacg      840
gccgctaagc tcatcgccct cgctgccgca agcctgctcc tcgccggtgg cggccgcctg      900
ccgctgctac agccgttcct gccacagctt ggtcgagcc gctcatgctg tcgccgcctc       960
tgcggctact gccgctttag gcggacttgc gggtggcggc ggagaccagg ggcttggcag     1020
ccgaggtctt ggaggccgag gcaccgttgc cgttgccgtt ggaggcagcg ccgttctccg     1080
aggtcgaggt ggtggaggcc tcaccggcca gcttgaggcc agcggtcttg gcttggcgg     1140
tggcgggcag ggcgggcttg taggtggtca ccttgggggt ggcggcggcg ggcgaggggc     1200
ccgagggggt ggtcgcgcgc cacgcgccca tggcggggc ggtggtgccg accttgggcg      1260
cggcggcgcc gttgccctcc acggaggcgg acacgggctt cagggtgttg ggggcgtagg     1320
acacggcggg caggtcgccg gggatcttct cggcaacggg caccttgatc tcctccttct     1380
tggcggtggc cacgccgccc ttgccgtaca ccacctcctc cagcaggccc tcccacttct     1440
gggcgggctt ggaccaggac aggtcctggc tgatgcagtt ggccaccatc tcggggtagc     1500
ggccgcccgc aaacacctcg ctggcacggc gcacggtggc ggccagggcg tcggcgtcag     1560
cctcgtccag cttgtcgggg ttcagggcgc ccatgtggaa gccggtgacg ccctccttga     1620
cggtgtcgac caggccgccg gtggaggcta ccacgggcac ggtaccgtag tgcatggcgt     1680
gcagctggat caggccgcag ggctcgaagc gcgagggcac cagcatgaag tcggcgccgg     1740
cggtgagcat gtgcgccagg ggcgccgaga acttgaccac gcccttggcg cggcccttgt     1800
acttggtgcc gatggcgttc accagcttct cgtaggcggc cttgccggta cccaggatgg     1860
cgatctgcac cttgggggtg gccaggatct tgggcagggg ggccaggatg atgtccacac     1920
ccttctgctc ctccaggcgg ccgatgaagg cgaacagggg ggcggtgggg tccacaggca     1980
ggcccagctc ggcctgcagg gcctccttgg cggcggcctt gccggcgtag acgctgttct     2040
ggtcgtaggg cgcagacagg aacttgtcgg tcttggggtt ccactcctca atgtccatgc     2100
cgttcacaat gccctcaatg cccttggcgc ggatgacggt gtccagctcc acaccgccgg     2160
cggcatcggc agcgatctcg gtcgcgtagt tgggcgacac agtcaccagc ttgtcggcgg     2220
cgataatgcc cccttcagc cagttgatct tcttgtaggt cttcccgtc agcggggct       2280
tctcgtcctc ctccatgggg gtggcctcag tgtaaaccTt ggcatagccg tccgagaagg     2340
ccagcttgtc aaaggcggcc tggggcagct tcgtgtcctt gaaagcctcc tcccacatgc     2400
ggccctggaa ggcgatgttg tggatagcca gcaccgactt ggccttggtg aactggccct     2460
tgggctggta ctcgtccttc agcaggacgg caccagggc ggagtgccag tcgttggcca     2520
cgaagacgca gtcctcgccg gggccgaagg gcagcacgcg ggcagcctca atagcggcct     2580
tgcagaacag ggcgaagcgc ttgtggttgt ccaggtagtc agcgccggag cggggccgt     2640
acagcttgga gccggtcttg ccccagacct tggccaggaa ccaggggtgg tcaatccaca     2700
```

-continued

```
cgcggtgcac gcccttcttg atggagtgga agtagcggac cttctcgccc atgatgtcca    2760
cgaccaccga ggtgtcccag gcgtcagcgt actggtcgta gcgaggggca atggtcatga    2820
cgcggtggcc gcgcttgacc agctcaatag gcaggccacc agtcacatcg cccaggccgc    2880
ccgtcttgga ccaaggggcg acctcagcag caaccatcac gatgtccagc gcgcaagtgg    2940
caccagtggc accagtaaca gccgagcgcg aggtggactt gcgtgcggag ccacgagcaa    3000
gctcacgcag cagctggttc gcggtcttct tgacaccgaa cgacgcggca ttgatgacga    3060
taggacgcgc gctgctgggg cggctggtag aggcaacagc catacgctcc gcctggc      3117
```